United States Patent
Alaoui-Jamali et al.

(10) Patent No.: US 9,085,598 B2
(45) Date of Patent: Jul. 21, 2015

(54) COMPOUNDS TARGETING THE CELL INVASION PROTEIN COMPLEX, THEIR PHARMACEUTICAL COMPOSITIONS AND METHODS OF USE THEREOF

(71) Applicants: THE ROYAL INSTITUTE FOR THE ADVANCEMENT OF LEARNING/MCGILL UNIVERSITY, Montreal (CA); OCEAN UNIVERSITY OF CHINA, Qingdao (CN)

(72) Inventors: Moulay A. Alaoui-Jamali, Outremont (CA); Krikor Bijian, Laval (CA); Jiang Tao, Qingdao (CN)

(73) Assignees: The Royal Institution for the Advancement of Learning/McGill University, Montreal (CA); Ocean University of China, Qingdao (CN)

( * ) Notice: Subject to any disclaimer, the term of this patent is extended or adjusted under 35 U.S.C. 154(b) by 0 days.

(21) Appl. No.: 14/354,871

(22) PCT Filed: Oct. 26, 2012

(86) PCT No.: PCT/CA2012/000997
§ 371 (c)(1),
(2) Date: Apr. 28, 2014

(87) PCT Pub. No.: WO2013/059927
PCT Pub. Date: May 2, 2013

(65) Prior Publication Data
US 2014/0256659 A1 Sep. 11, 2014

Related U.S. Application Data

(60) Provisional application No. 61/552,570, filed on Oct. 28, 2011.

(51) Int. Cl.
C07H 19/02 (2006.01)
C07H 13/02 (2006.01)
C07H 15/26 (2006.01)
C07H 15/203 (2006.01)
C07H 99/00 (2006.01)

(52) U.S. Cl.
CPC ............... C07H 19/02 (2013.01); C07H 13/02 (2013.01); C07H 15/203 (2013.01); C07H 15/26 (2013.01); C07H 99/00 (2013.01)

(58) Field of Classification Search
None
See application file for complete search history.

(56) References Cited

FOREIGN PATENT DOCUMENTS

CA 2600134 9/2006

OTHER PUBLICATIONS

Dallacker et al., Chemiker-Zeitung, 1991, 115(5), pp. 135-9.*
Bijian, et al., Eur J Med Chem. 48:143-52, 2012.
Dallacker, et al., Chemiker-Zeitung. 115(5):135-9, 1991.
Duxbury, et al., Biochem Biophys Res Comm. 311:786-92, 2003.
Hauck, et al., Cancer Res. 61:7079-90, 2001.
Hirayama, et al., Chem Pharm Bull. 32(10):4237-4240, 1984.
Kim & Feldman, J Biol Chem. 277:27393-400, 2002.
Kobayashi, et al., Chem Pharm Bull. 33(2):697-703, 1985.
Pai, et al., Life Sciences. 69:3055-71, 2001.
Schaller, et al., Mol Cell Biol. 13(2):785-91, 1993.
Search Report in International Application No. PCT/CA2012/000997 filed Oct. 26, 2012.
Slack, et al., Oncogene, 20:1152-63, 2001.
Slack-Davis, et al., J Biol Chem. 282:14845-52, 2007.
Sood, et al., Am J Pathol. 165(4):1087-95, 2004.
Winum, et al., Il Farmaco. 56:319-324, 2001.
Yu, et al., Helvetica Chimica Acta. 85:9-18, 2002.
Zhang, et al., Synth Comm. 40:3438-46, 2010.

* cited by examiner

*Primary Examiner* — Traviss C McIntosh, III
(74) *Attorney, Agent, or Firm* — Norton Rose Fulbright US LLP

(57) ABSTRACT

The present application relates to the compounds of formula I (I) as well as their use for inhibiting at least one of AKT-1, FAK and PKCα and in the treatment and/or prevention of metastatic diseases.

17 Claims, 3 Drawing Sheets

COMPOUNDS TARGETING THE CELL INVASION PROTEIN COMPLEX, THEIR PHARMACEUTICAL COMPOSITIONS AND METHODS OF USE THEREOF

CROSS-REFERENCE TO RELATED APPLICATION

This application is a national phase application under 35 U.S.C. 371 of International Application No. PCT/CA2012/000997 filed Oct. 26, 2012, which claims priority from U.S. provisional patent application 61/552,570 filed on Oct. 28, 2011. The entire contents of each of the above-referenced disclosures is specifically incorporated herein by reference without disclaimer.

FIELD OF THE DISCLOSURE

The present invention relates to novel compounds, compositions containing same and methods for treating metastatic disease or for the treatment or prevention of disease conditions using said compounds.

BACKGROUND OF THE DISCLOSURE

The progression of primary cancer to metastases is an ominous event in patients at primary diagnosis, and is an important cause of morbidity and mortality. Presently used targeted therapies for metastatic disease such as herceptin/trastuzumab (the humanized therapeutic antibody against ErbB-2/Her-2 receptor) combined with chemotherapy have demonstrated modest improvement over more traditional therapies. This has also been observed for other metastatic diseases such as colorectal, melanoma, pancreatic, and kidney. Therefore, there is a need to develop treatment that selectively targets rate-limiting signaling driving the early process of cancer cell invasion.

An early event by which cancer cells acquire autonomous motile properties is driven by focal adhesion (FA) signaling, which is essential for cell-substrate generating forces needed for the coordination of the entire process of cancer cell migration and invasion. Central to FA signaling is the focal adhesion kinase (FAK) and its homologue Pyk2, two kinases activated by integrins and a number of growth factors receptors, including ErbB-2/Her2 receptor. These proteins also serve as scaffolding proteins that mediate multiple protein-protein interactions critical for cancer cell invasion, e.g. cell survival, anoikis (programmed cell death induced by cell detachment from the extracellular matrix, which is probably regulated by PI3K signaling), angiogenesis, and survival of invasive cells in new environments. For instance, the non-catalytic domains of FAK contain binding motifs for Src kinases and interact with other partners, including PI3K, Crk, PLCλ, p130Cas, Grb7, and paxillin; these interactions represent the core of FA signaling. Members of this network, including FAK, PKCα and Akt-1 are hyperactivated in some invasive cancers, and their inhibition using genetic approaches, e.g. RNA interference, or chemical inhibitors reduced metastasis formation. However, approaches targeting these proteins individually have proven of limited efficacy due in part to compensatory signaling loops that can overcome a single target inhibition. As such, the field of drug discovery is moving towards a multitargeting approach to target multifactorial diseases such as cancer.

Pyrimidine and pyridinone derivatives have been reported to inhibit focal adhesion kinase (FAK) and its homologue Pyk2, two FA signaling proteins, or FAK and IGFR-1R receptor. Nonetheless, results for some of these agents have revealed only modest disease stabilization thus far.

SUMMARY

In an aspect of the disclosure, there is provided a compound of formula I:

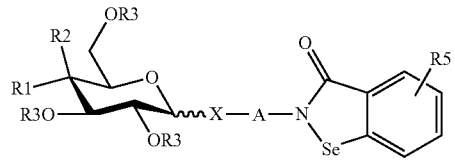

or a pharmaceutically acceptable salt or solvate thereof,
wherein X is —O—, —OCO—, —NR10CO—, or absent;
A is arylene, C1-7 alkylene or a bond;
R10 is H or C1-3 alkyl;
R1 and R2 are each independently H, OR3 or a moiety selected from the following structures:

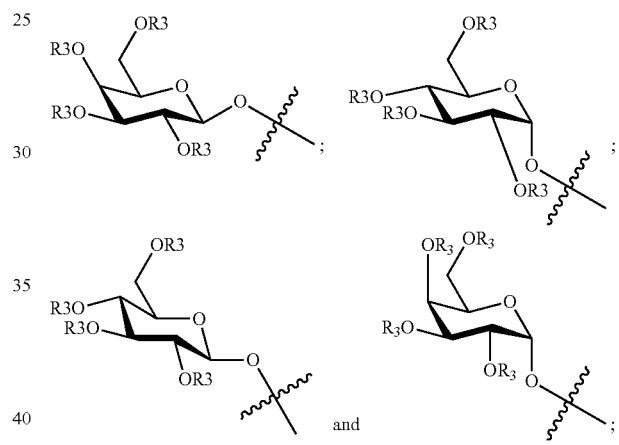

R3 are each independently H or a protecting group;
provided that one of R1 or R2 is H; and
R5 is one or more optional substituent.

In a further aspect, there is provided a pharmaceutical composition comprising a compound as defined herein or a pharmaceutically acceptable salt or solvate thereof, and an acceptable excipient.

In an aspect, there is provided a method for inhibiting at least one of FAK, AKT-1 and PKC-α in a subject in need thereof, said method comprising administering a therapeutically effective amount of the compound as defined herein or a pharmaceutically acceptable salt or solvate thereof or the pharmaceutical composition as defined herein to the subject thereby inhibiting the at least one of FAK, AKT-1 and PKC-α. 15. In an embodiment, the subject is a human.

In still a further aspect, there is provided a method for treating or preventing a metastatic disease in a subject in need thereof, said method comprising administering a therapeutically effective amount of the compound as defined herein, or a pharmaceutically acceptable salt or solvate thereof or the pharmaceutical composition as defined herein to the subject thereby treating or preventing the metastatic disease. In an embodiment, the subject is a human. In yet another embodiment, the metastatic cancer is a metastatic breast cancer or a metastatic colon cancer.

In still a further aspect, there is provided a method for limiting the progression of a metastatic disease in a subject in need thereof, said method comprising administering a therapeutically effective amount of the compound as defined herein, or a pharmaceutically acceptable salt or solvate thereof or the pharmaceutical composition as defined herein to the subject thereby limiting the progression of the metastatic disease.

In a further aspect, there is provided a use of the compound as defined herein or a pharmaceutically acceptable salt or solvate thereof for inhibiting at least one of FAK, AKT-1 and PKC-α or in the manufacture of a medicament for inhibiting at least one of FAK, AKT-1 and PKC-α.

In a further aspect, there is provided a use of the compound as defined herein or a pharmaceutically acceptable salt or solvate thereof for treating or preventing a metastatic disease or in the manufacture of a medicament for treating or preventing a metastatic disease. In an embodiment, the metastatic cancer is a metastatic breast cancer or a metastatic colon cancer.

In a further aspect, there is provided a use of the compound as defined herein or a pharmaceutically acceptable salt or solvate thereof for limiting the progression of a metastatic disease or in the manufacture of a medicament for limiting the progression of a metastatic disease. In an embodiment, the metastatic cancer is a metastatic breast cancer or a metastatic colon cancer.

In a further aspect, there is provided a method for preparing a pharmaceutical composition comprising the step of bringing into association the compound as defined herein and pharmaceutically acceptable carriers.

DESCRIPTION OF EMBODIMENTS

Figure 1A:
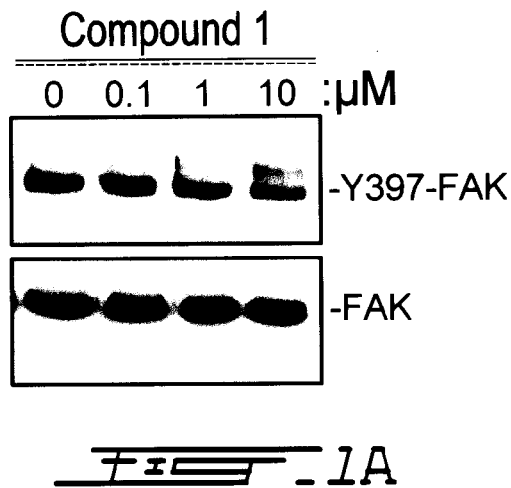
FIG. 1 shows that a compound of the disclosure inhibits FAK phosphorylation and kinase activity in intact cells. A) Representative western blot analysis of total cell extracts of MDA-231 cells treated with increasing concentrations of compound 1, as indicated. Inhibition of FAK activation, as demonstrated by FAK (Tyr-397) phosphorylation is observed at 10 μM of compound 1. B) FAK was immunoprecipitated from lysates of MDA-231 cells treated with indicated concentration of compound 2d and were incubated with [γ-$^{32}$P]-ATP in order to monitored for FAK kinase activity. Significant inhibition of FAK kinase activity was observed at 10 μM (*P<0.05) and 50 μM (**P<0.01) of compound 1, as compared to untreated controls (N=4). Ebselen was unable to inhibit FAK kinase activity at 50 μM.

In accordance with one embodiment, the disclosure provides a compound of formula Ia:

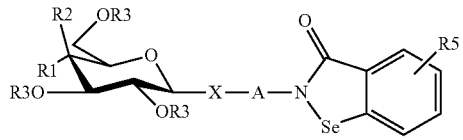

In another embodiment, there is also provided a compound of formula II

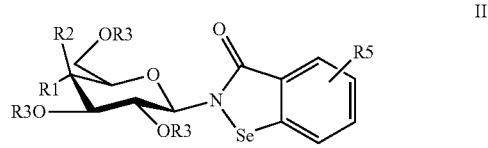

or a pharmaceutically acceptable salt or solvate thereof.

In accordance with one embodiment, there is provided a compound of formula Ia wherein A is C1-7alkylene. In a further embodiment, A is a C1-3alkylene. In still a further embodiment, A is methylene, ethylene or propylene.

In another embodiment, there is provided a compound of formula III

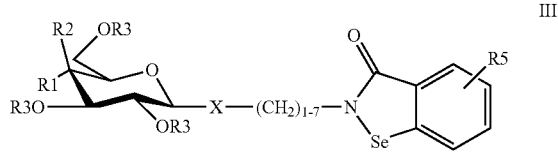

or a pharmaceutically acceptable salt or solvate thereof.

In another embodiment, there is provided a compound of formula IIIa, formula IIIb or formula IIIc

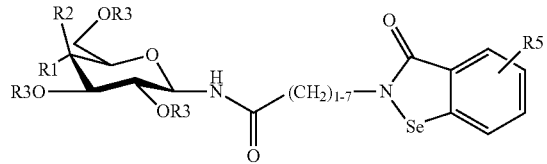
IIIa

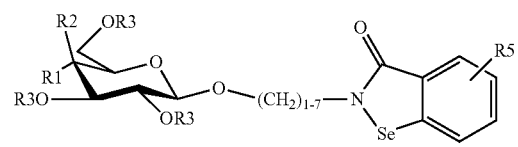
IIIb

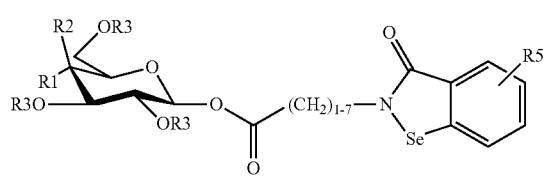
IIIc or a pharmaceutically acceptable salt or solvate thereof.

In accordance with one embodiment, there is provided a compound of formula Ia wherein A is C6arylene. In a further embodiment, A is a phenylene.

In yet another embodiment, there is provided a compound of formula IV

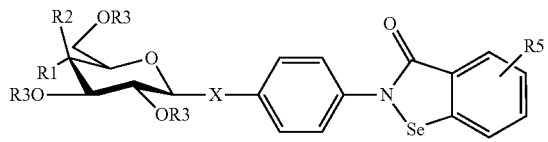
IV or a pharmaceutically acceptable salt or solvate thereof.

In another embodiment, there is provided a compound of formula IVa, formula IVb or formula IVc

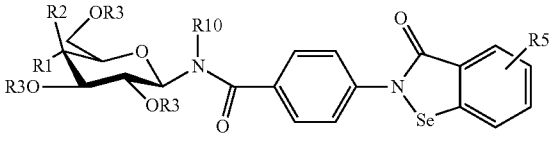
IVa

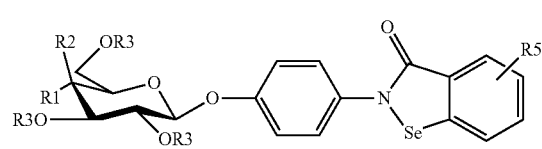
IVb

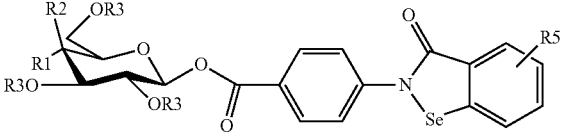
IVc or a pharmaceutically acceptable salt or solvate thereof.

In one embodiment, there is provided a compound of formula I, Ia, II, III, IV, IIIa, IIIb, IIIc, IVa, IVb or IVc or a pharmaceutically acceptable salt or solvate thereof, wherein R3 is acetyl or H.

In another embodiment, there is provided a compound of formula III, IV, IIIa or IVa or a pharmaceutically acceptable salt or solvate thereof, wherein R10 is H.

In one embodiment, there is provided a compound of formula I, Ia, II, III, IV, IIIa, IIIb, IIIc, IVa, IVb or IVc or a pharmaceutically acceptable salt or solvate thereof, wherein R1 is OR3.

In one embodiment, there is provided a compound of formula I, Ia, II, III, IV, IIIa, IIIb, IIIc, IVa, IVb or IVc or a pharmaceutically acceptable salt or solvate thereof, wherein R2 is OR3.

In one embodiment, there is provided a compound of formula I, Ia, II, III, IV, IIIa, IIIb, IIIc, IVa, IVb or IVc or a pharmaceutically acceptable salt or solvate thereof, wherein R1 is OR3 and R3 is H or acetyl.

In one embodiment, there is provided a compound of formula I, Ia, II, III, IV, IIIa, IIIb, IIIc, IVa, IVb or IVc or a pharmaceutically acceptable salt or solvate thereof, wherein R2 is OR3 and R3 is H or acetyl.

In one embodiment, there is provided a compound of formula I, Ia, II, III, IV, IIIa, IIIb, IIIc, IVa, IVb or IVc or a pharmaceutically acceptable salt or solvate thereof, wherein R1 is

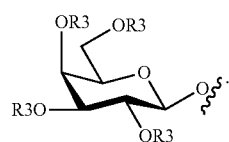

In one embodiment, there is provided a compound of formula I, Ia, II, III, IV, IIIa, IIIb, IIIc, IVa, IVb or IVc or a pharmaceutically acceptable salt or solvate thereof, wherein R1 is

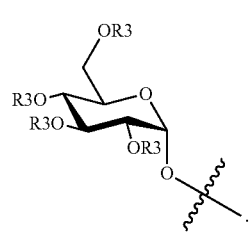

In another embodiment, there is provided a compound of formula I, Ia, II, III, IV, IIIa, IIIb, IIIc, IVa, IVb or IVc or a pharmaceutically acceptable salt or solvate thereof, wherein R1 is

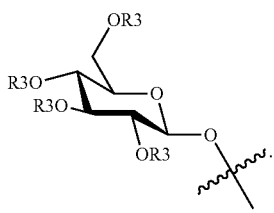

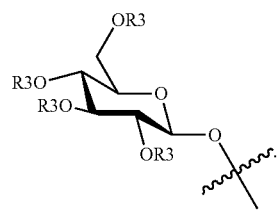

In another embodiment, there is provided a compound of formula I, Ia, II, III, IV, IIIa, IIIb, IIIc, IVa, IVb or IVc or a pharmaceutically acceptable salt or solvate thereof, wherein R1 is In yet another embodiment, there is provided a compound of formula I, Ia, II, III, IV, IIIa, IIIb, IIIc, IVa, IVb or IVc or a pharmaceutically acceptable salt or solvate thereof, wherein R2 is

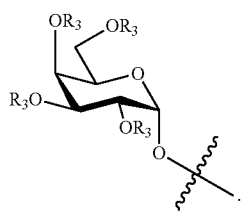

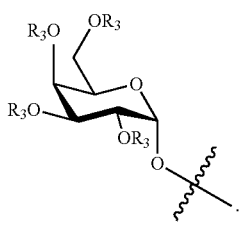

In another embodiment, there is provided a compound of formula I, Ia, II, III, IV, IIIa, IIIb, IIIc, IVa, IVb or IVc or a pharmaceutically acceptable salt or solvate thereof, wherein R2 is In one embodiment, there is provided a compound of formula I, Ia, II, III, IV, IIIa, IIIb, IIIc, IVa, IVb or IVc or a pharmaceutically acceptable salt or solvate thereof, wherein R1 is

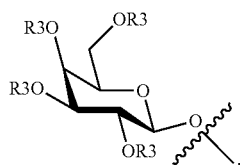

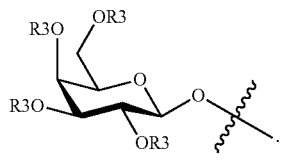

In another embodiment, there is provided a compound of formula I, Ia, II, III, IV, IIIa, IIIb, IIIc, IVa, IVb or IVc or a pharmaceutically acceptable salt or solvate thereof, wherein R2 is and R3 is H or acetyl.

In one embodiment, there is provided a compound of formula I, Ia, II, III, IV, IIIa, IIIb, IIIc, IVa, IVb or IVc or a pharmaceutically acceptable salt or solvate thereof, wherein R1 is

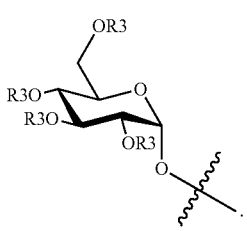

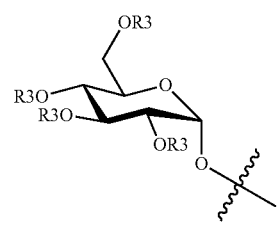

In yet another embodiment, there is provided a compound of formula I, Ia, II, III, IV, IIIa, IIIb, IIIc, IVa, IVb or IVc or a pharmaceutically acceptable salt or solvate thereof, wherein R2 is and R3 is H or acetyl.

In another embodiment, there is provided a compound of formula I, Ia, II, III, IV, IIIa, IIb, IIIc, IVa, IVb or IVc or a pharmaceutically acceptable salt or solvate thereof, wherein R1 is

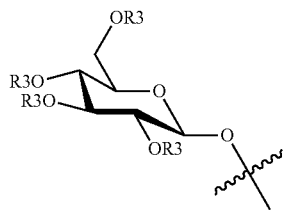

and R3 is H or acetyl.

In another embodiment, there is provided a compound of formula I, Ia, II, III, IV, IIIa, IIIb, IIIc, IVa, IVb or IVc or a pharmaceutically acceptable salt or solvate thereof, wherein R1 is

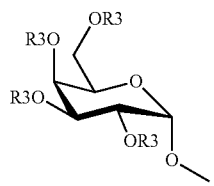

and R3 is H or acetyl.

In another embodiment, there is provided a compound of formula I, Ia, II, III, IV, IIIa, IIIb, IIIc, IVa, IVb or IVc or a pharmaceutically acceptable salt or solvate thereof, wherein R2 is

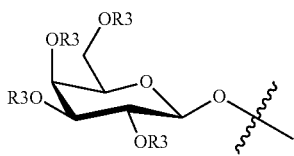

and R3 is H or acetyl.

In another embodiment, there is provided a compound of formula I, Ia, II, III, IV, IIIa, IIIb, IIIc, IVa, IVb or IVc or a pharmaceutically acceptable salt or solvate thereof, wherein R2 is

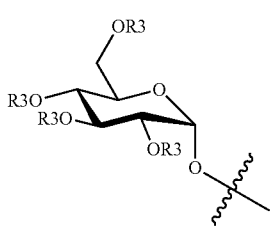

and R3 is H or acetyl.

In yet another embodiment, there is provided a compound of formula I, Ia, II, III, IV, IIIa, IIIb, IIIc, IVa, IVb or IVc or a pharmaceutically acceptable salt or solvate thereof, wherein R2 is

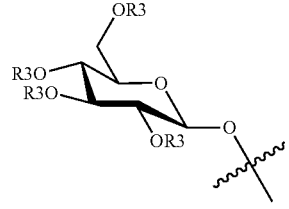

and R3 is H or acetyl.

In yet another embodiment, there is provided a compound of formula I, Ia, II, III, IV, IIIa, IIIb, IIIc, IVa, IVb or IVc or a pharmaceutically acceptable salt or solvate thereof, wherein R2 is

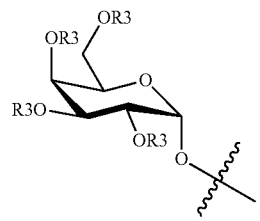

and R3 is H or acetyl.

In accordance with another embodiment, there is provided a compound of the present disclosure or a pharmaceutically acceptable salt or solvate thereof, wherein R5 is one or more optional substituent and each is independently selected from one or more substituent each independently selected from halogen, amino, amidino, amido, azido, cyano, guanido, hydroxyl, nitro, nitroso, urea, —OS(O)$_2$R20, —OS(O)$_2$OR21, —S(O)$_2$OR21, S(O)$_{0-2}$R21, —OP(O)OR22OR23, —P(O)OR22OR23, C1-6alkyl, C6-10aryl-C1-6alkyl, C6-10aryl, C1-6alkoxy, C6-10aryl-C1-6alkyloxy, C6-10aryloxy, 3-10 membered heterocycle, —C(O)R24, —C(O)OR24, —NR25C(O)R26, —C(O)NR25R27 and —SO$_2$NR24R27.

Alternatively, R5 is one or more optional substituent each independently selected from halogen, amino, cyano, hydroxyl, nitro, C1-6alkyl, C6-10aryl-C1-6alkyl, C6-10aryl, C1-6alkoxy, C6-10aryl-C1-6alkyloxy, C6-10aryloxy, 3-10 membered heterocycle, —C(O)R24, —C(O)OR24, —NR25C(O)R26, —C(O)NR25R27 and —SO$_2$NR24R27.

R20 is each independently C1-6 alkyl, C6-10 aryl or 3-10 membered heterocycle;

R21 is each independently H, C1-6 alkyl, C6-10 aryl or 3-10 membered heterocycle;

R22 and R23 are each independently H or C1-6 alkyl;

R24 and R27 are each independently H, C1-6 alkyl, C6-10 aryl, C6-10aryl-C1-6alkyl or 3-10 membered heterocycle;

or R24 and R27 are taken together with the atoms to which they are attached to form a 3 to 10 membered heterocycle.

R25 is H or C1-6 alkyl; and

R26 is each independently H, C1-6 alkyl, C6-10 aryl, C6-10aryl-C1-6alkyl or 3-10 membered heterocycle;

or R25 and R26 are taken together with the atoms to which they are attached to form a 3 to 10 membered heterocycle.

In another embodiment, there is also provided a compound of formula II

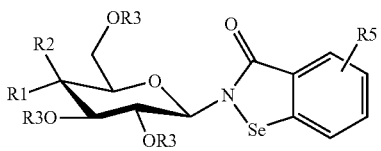

R1 is

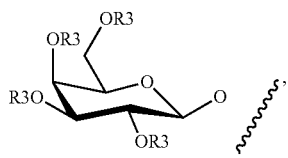

R2 is H, R3 is H or acetyl and R5 is H. In a further embodiment, R3 in the previous formula is acetyl. In a further embodiment, R3 in the previous formula is H.

In another embodiment, there is also provided a compound of formula

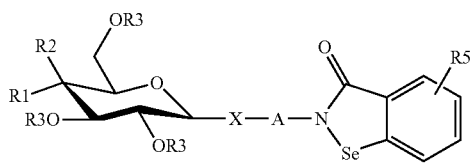

wherein X is —NHCO— A is —(CH$_2$)$_{1-3}$—; R1 is OR3, R2 is H; R3 is H or acetyl. In a further embodiment of the formula above, X is —NHCO—; A is —(CH$_2$)$_3$—; R1 is OR3, R2 is H; R3 is H or acetyl. In a further embodiment, R3 is acetyl. Still in a further embodiment, R3 is H.

The term "alkyl" represents a linear or branched moiety. Examples of "alkyl" groups include but are not limited to methyl, ethyl, propyl, isopropyl, butyl, isobutyl, sec-butyl, tert-butyl, pentyl, isopentyl, neopentyl, tert-pentyl, hexyl, isohexyl or neohexyl. The term "alkyl" is also meant to include alkyls in which one or more hydrogen atom is replaced by a halogen, ie. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. The term "alkylene" is an alkyl residue having two points of attachment.

The terms "alkoxy," represent an alkyl, moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy.

The term "aryl" represents a carbocyclic moiety containing at least one benzenoid-type ring (i.e., may be monocyclic or polycyclic), Examples include but are not limited to phenyl, tolyl, dimethylphenyl, aminophenyl, anilinyl, naphthyl, anthryl, phenanthryl or biphenyl. The term "arylene" is an aryl residue having two points of attachment.

The term "aryloxy" represents an aryl moiety, which is covalently bonded to the adjacent atom through an oxygen atom. Examples include but are not limited to phenoxy, dimethylphenoxy, aminophenoxy, anilinoxy, naphthoxy, anthroxy, phenanthroxy or biphenoxy.

The term "arylalkyl" represents an aryl group attached to the adjacent atom by an alkyl.

Examples include but are not limited to benzyl, benzhydryl, trityl, phenethyl, 3-phenylpropyl, 2-phenylpropyl, 4-phenylbutyl and naphthylmethyl.

The term "arylalkyloxy" represents an arylalkyl moiety, which is covalently bonded to the adjacent atom through an oxygen atom. Examples include but are not limited to benzyloxy, benzhydroxy, trityloxy, phenethyloxy, 3-phenylpropoxy, 2-phenylpropoxy, 4-phenylbutoxy and naphthylmethoxy.

The term "heterocycle" represents a 3 to 11 membered optionally substituted saturated, unsaturated, partially saturated or aromatic cyclic moiety wherein said cyclic moiety is interrupted by at least one heteroatom selected from oxygen (O), sulfur (S) or nitrogen (N).

Heterocycles may be monocyclic or polycyclic rings. Heterocycles may be 3 to 6 membered monocyclic ring or 5 to 6 membered monocyclic ring. Heterocycles may be 7 to 12 membered bicyclic ring or 9 to 10 membered bicyclic ring. Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The expression "protecting group" includes any suitable protecting groups for protecting the indicated moiety. Examples of "protecting group" for protecting hydroxyl moiety include but are not limited to benzyl, substituted benzyl, para-methoxybenzyl (PMB), trityl, allyl, pivaloyl, benzoyl, acetyl, chloroacetyl, levulinoyl, methoxymethyl (MOM), methoxytrityl (MMT), methylthiomethyl, isopropylidene, benzylidene, butane diacetal and silyl groups such as trimethylsilyl (TMS), tert-butyldimethylsilyl (TBDMS), tert-butyldimethyloxymethylsilyl (TOMS), triisopropylsilyl (TIPS) and tert-butyldiphenylsilyl (TBDPS). More examples of protecting groups can be found in Green et al., "Protective Groups in Organic Chemistry", (Wiley, 4$^{th}$ ed. 2007) and Harrison et al. "Compendium of Synthetic Organic Methods" (John Wiley and Sons, 1996).

"Halogen atom" is specifically a fluorine atom, chlorine atom, bromine atom or iodine atom.

The term "independently" means that a substituent can be the same or a different definition for each item.

The symbol "  " used in the present disclosure represents a chemical bond which has no specified absolute stereochemistry.

The excipient(s) must be "pharmaceutically acceptable" in the sense of being compatible with the other ingredients of the formulation and not being deleterious to the recipient thereof.

In another embodiment, the present invention provides a combination comprising a therapeutically effective amount of a compound, as defined herein, and a therapeutically effective amount of at least one or more therapeutic agents useful in the method of the present to disclosure.

It will be clear to a person of ordinary skill that if a further additional therapeutic agent is required or desired, ratios will be readily adjusted. It will be understood that the scope of combinations described herein is not particularly limited, but includes in principles any therapeutic agent compatible and useful in the context of the present disclosure including the prevention and treatment of metastatic disease such as cancer. Examples of further additional therapeutic agent includes without limitation imatinib, taxol, cisplatin, doxorubicine, vinblastine, zoledronate (or in conjunction with antimetastatic agents, antiangiogenic agents such as avastatin, and antiapoptotic compounds such as Valcade).

It will be appreciated that the amount of a compound of the disclosure required for use in treatment will vary not only with the particular compound selected but also with the route of administration, the nature of the condition for which treatment is required and the age and condition of the patient and will be ultimately at the discretion of the attending physician. Generally, the amount administered will be empirically determined, typically in the range of about 10 μg to 1000 mg/kg body weight of the recipient.

The desired dose may conveniently be presented in a single dose or as divided dose administered at appropriate intervals, for example as two, three, four or more doses per day.

Pharmaceutical compositions include, without limitation, those suitable for oral (including buccal and sub-lingual), transdermal, or parenteral (including intramuscular, sub-cutaneous and intravenous) administration or in a form suitable for administration by inhalation.

The formulations may, where appropriate, be conveniently presented in discrete dosage units and may be prepared by any of the methods well known in the art of pharmacy. The methods for preparing a pharmaceutical composition can include the steps of bringing into association the compound as defined herein and pharmaceutically acceptable excipients and then, if necessary, shaping the product into the desired formulation, including applying a coating when desired.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations as defined herein may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

Compositions suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation, the compounds and combinations as defined herein may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

Further description of methods suitable for use in preparing pharmaceutical compositions for use in the present disclosure and of ingredients suitable for use in said compositions is provided in Remington's Pharmaceutical Sciences, 18(th) edition, edited by A. R. Gennaro, Mack Publishing Co., 1990.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can to contain more than one chiral centres. The compounds of the present invention may thus exist in the form of different diastereomers. All such diastereomers and mixtures thereof are included within the scope of the invention. The single diastereomer can be obtained by method well known in the art, such as HPLC, crystalisation and chromatography.

There is also provided pharmaceutically acceptable salts of the compounds of the present invention. What is meant by the term pharmaceutically acceptable salts of the compounds is that they are derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

The pharmaceutically acceptable salts of the compounds of this disclosure can be synthesized from the compounds of this disclosure which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The term "solvate" means that compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

When there is a sulfur atom present, the sulfur atom can be at different oxidation levels, ie. S, SO, or $SO_2$. All such oxidation levels are within the scope of the present invention.

When there is a nitrogen atom present, the nitrogen atom can be at different oxidation levels, ie. N or NO. All such oxidation levels are within the scope of the present invention.

Non-limiting examples of compounds in accordance with formula I include

| No. | Compound |
|---|---|
| 1 | (structure) |
| 2 | (structure) |
| 3 | (structure) |
| 4 | (structure) |
| 5 | (structure) |

-continued

| No. | Compound |
|---|---|
| 6 | *galactose-glucose disaccharide linked to N-benzo[d][1,2]selenazol-3(2H)-one* |
| 7 | *per-acetylated galactose-glucose disaccharide with acetamido-CH₂-benzo[d][1,2]selenazol-3(2H)-one linker* |
| 8 | *per-acetylated disaccharide with acetamido-CH₂-benzo[d][1,2]selenazol-3(2H)-one linker* |
| 9 | *galactose with acetamido-CH₂-benzo[d][1,2]selenazol-3(2H)-one* |
| 10 | *per-acetylated galactose with acetamido-CH₂-benzo[d][1,2]selenazol-3(2H)-one* |
| 11 | *per-acetylated glucose with acetamido-CH₂-benzo[d][1,2]selenazol-3(2H)-one* |
| 12 | *galactose with butanamido-(CH₂)₃-benzo[d][1,2]selenazol-3(2H)-one* |
| 13 | *per-acetylated galactose with butanamido-(CH₂)₃-benzo[d][1,2]selenazol-3(2H)-one* |

| No. | Compound |
|---|---|
| 14 | |
| 15 | |
| 16 | |
| 17 | |
| 18 | |
| 19 | |
| 20 | |
| 21 | |

-continued

| No. | Compound |
|---|---|
| 22 | [structure: glucose (OH) linked via NH-C(=O) to phenyl-N-benzisoselenazol-3(2H)-one] |
| 23 | [structure: galactose (OH) linked via NH-C(=O) to phenyl-N-benzisoselenazol-3(2H)-one] |
| 24 | [structure: peracetylated sugar (OAc) linked via NH-C(=O) to phenyl-N-benzisoselenazol-3(2H)-one] |
| 25 | [structure: peracetylated sugar (OAc) linked via O to phenyl-N-benzisoselenazol-3(2H)-one] |
| 26 | [structure: sugar (OH) linked via O to phenyl-N-benzisoselenazol-3(2H)-one] |
| 27 | [structure: peracetylated disaccharide linked via NH-C(=O) to phenyl-N-benzisoselenazol-3(2H)-one] |
| 28 | [structure: peracetylated sugar linked via O-C(=O) to phenyl-N-benzisoselenazol-3(2H)-one] |

-continued

| No. | Compound |
|---|---|
| 29 | (structure) |
| 30 | (structure) |
| 31 | (structure) | or a pharmaceutically acceptable salt thereof.

FAK is a central focal adhesion and adapter protein that interacts with partners, including PI3K/Akt and PKCα and is implicated in focal adhesion and survival signaling. Focal adhesion and survival signaling are important cellular events in cancer cell invasion beyond primary sites, e.g. the dissemination of metastatic cells and the formation of metastasis. Therefore, at least some of the compounds described herein may advantageously provide selectivity towards at least one of FAK, Akt-1, and PKCα. In an embodiment, the compounds described herein may also advantageously provide selectivity toward at least two of the kinases, and yet, in a further embodiment, may further provide selectivity towards the three kinases. Such compounds could to also inhibit, to a lesser extent, the activity of other related enzymes such as, for example, Src, EGFR, ErbB2, IGFR, PDGFR, Abl1, Flt-3, and MAPKs. In some preferred embodiment, the compounds show little to no inhibitory activity towards at least one (and most preferably towards all) IGF1R, ABL1, Aurora A, Aurora B, CDK1/Cyclin B, DDR1, EGFR, EPHA1, FGFR1, FLT3, FYN, HER2, IKK-ε, INSR, LYN, MET, P38-γ, PAK1, PDGFRβ, PIM1, PLK4, RPS6KA4, SGK3, SRC, SYK, TIE1, TRKB, EGFR2, YES1.

The methods described herein can be useful for the inhibition of the activity of at least one of (or a combination thereof) of the following kinases: FAK, Akt-1, and PKCα. In some conditions, such as in metastatic diseases, pathological cell motility and invasion rely, in part, on the biological activity of these kinases. As such, the inhibition of at least one of (or a combination thereof) of FAK, Akt-1, and PKCα may be beneficial to limit the pathological cell motility and invasion. As used herein, the terms "inhibiting" and "inhibition" refer to the ability of the compounds to lower, and in some embodiments inhibit, the biological activity of the kinase(s) when compared to a control activity (in the absence of the compounds or in the presence of a control compound known not to modulate the activity of the kinase). The biological activity of the kinases can be, for example, their ability to phosphorylate one of their substrate. In an embodiment, the compounds described herein inhibit at least 25% of the activity of at least one (or a combination thereof) of FAK, Akt-1, and PKCα. In an embodiment, the compounds inhibit at least 50% of the activity of at least one (or a combination thereof) of FAK, Akt-1, and PKCα. In a further embodiment, the compounds inhibit at least 60% of the activity of at least one (or a combination thereof) of FAK, Akt-1, and PKCα. In another embodiment, the compounds inhibit at least 75% of the activity of at least one (or a combination thereof) of FAK, Akt-1, and PKCα.

In the art, the term "metastasising" usually refers to a multi-step cascade involving migration of tumor cells from their site of origin (e.g. the primary tumor), the evasion of host immune systems and resulting in the seeding of metastatic cells (usually referred to as metastases) in distinct organs or tissues. More specifically, the formation of metastases involves the acquisition by primary tumor cells of characteristics to facilitate migration such as the breakdown of extracellular matrix components, the ability to upregulate the migration of the cells, etc. Such cellular characteristics may be linked to the modulation of the activity of various kinases, such as FAK, Akt-1, and/or PKCα. In an embodiment, the inhibition of at least one of (or a combination thereof) FAK, Akt-1, and PKCα can be associated with the prevention or treatment of a metastatic disease, the reduction in the number and/or size of metatases as well as the reduction in the number of organs/tissues colonized by metastases.

As used herein, the term "metastatic disease" refer to conditions which can spread to another organ or tissue (or part thereof) to another non-adjacent organ or tissue (or part thereof). In an embodiment, the metastatic disease refers to a cancer metastatic disease, e.g. the establishment of metastases. Some cancer cells can acquire the ability to penetrate the walls of lymphatic and/or blood vessels, after which they are able to circulate through the bloodstream (circulating tumor cells) to other sites and tissues in the body. This process is usually known (respectively) as lymphatic or hematogenous spread. After the tumor cells come to rest at another site, they re-penetrate through the vessel or walls, continue to multiply, and eventually another clinically detectable tumor is formed. This new tumor is known as a metastatic (or secondary or tertiary) tumor. When tumor cells metastasize, the new tumor is called a secondary or metastatic tumor, and its cells are like those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

It will be clear to a person skilled in the art that metastatic diseases include, but are not limited to, cancer metastatic spread derived from a carcinoma, a sarcoma, a lymphoma, a leukemia, a germ cell tumor, and/or a blastoma. Metastatic diseases also includes metastatic spread from benign tumors. In an embodiment, the metastatic disease further include metastatic spread from cancerous and benign tumors from the bladder, the colon, the liver, the lung, (e.g. pleural mesothelioma, e.g. non small cell, e.g. small cell), the breast, the vagina, the ovaries, the pancreas, the kidney, the stomach, gastrointestinal tract, (e.g. gastrointestinal stromal tumor, e.g. the small intestine, e.g. the esophagus, e.g. the bile duct), the prostate, the head and neck, the peritoneal cavity, the thyroid, the bone, the brain, the central nervous system (e.g. glioblastoma, e.g. neuroblastoma), and/or melanoma. In another embodiment, the metastatic disease can be derived from a cancer of the blood, e.g. hematological cancer, e.g. leukemia, e.g. acute myeloid leukemia, e.g. chronic myeloid leukemia, e.g. chronic lymphatic leukemia, e.g. acute lymphatic leukemia, e.g. multiple myeloma e.g. lymphomas, and/or for use in treatment of myelodysplastic syndrome, systemic mastocytosis. In some embodiments, the metastatic disease is a metatastatic prostate cancer, breast cancer and/or colon cancer. In other embodiments, the metastatic disease is breast cancer and/or colon cancer.

The methods described herein are useful for the prevention or treatment of a metastatic disease. As used herein, the expression "prevention or treatment of a metastatic disease" refers to the ability of the compound to limit or lower the occurrence of the metastatic disease, limit the metastatic potential of the cancer and/or limit the number and dissemination of the metastases when compared to a control (in the absence of the compounds or in the presence of a control compound known not to modulate the metastatic disease). In another embodiment, the methods described herein can also be useful in the prevention of the appearance of symptoms associated with a metastatic disease or in limiting the severity of the symptoms associated with a metastatic disease.

The methods described herein can also be useful for limiting the progression of the metastatic disease. As used herein, the expression "limiting the progression of the metastatic disease" refers to the ability of the compound to delay or inhibit the appearance of metastases, limit the number of metastases, limit the size of the metastases and/or limit the number of organs or tissues containing metastases. In an embodiment, the methods described herein can also be useful in preventing the symptoms associated with the progression of metastatic disease or in limiting the severity of the symptoms associated with the progression of metastatic disease.

The binding mode of the compounds to each of these kinases has been investigated by molecular modelling studies of compound 1 in the ATP-binding pocket of the AKT-1, FAK and PKCα kinase domains.

Docking studies: Crystal structures of AKT1, FAK and PKCα in complex with their inhibitors (PDB entries: 3MVH, 2JKO and 3IW4, respectively) were utilized in the docking study after the bound inhibitors were taken out. Compound 1 was docked into the ATP-binding pocket of AKT1, FAK and PKCα, respectively, using software Gold v3.2 (The Cambridge Crystallographic Data Centre, Cambridge, U.K.) by Goldscore function and standard default parameter settings. The ligand is treated as fully flexible, whereas the proteins were kept rigid except that each Ser, Thr and Tyr hydroxyl group was allowed to rotate to optimize hydrogen-bonding to the ligand, whereas other parts of the protein were kept rigid. Compound 1 successfully fit into the ATP-binding pocket of all 3 kinases. Similar binding modes of compound 1 were observed during its interaction with AKT1 or PKCα, whereas a different predicted pose was obtained with FAK.

Abbreviations Used in the Description of the Preparation of the Compounds of the Present Disclosure:

ATP: Adenosine triphosphate; BSA: Bovine Serum Albumin; $CD_3OD$: Deuterated methanol; DCC: N,N'-dicyclohexylcarbodiimide; DMEM: Dulbecco's modified eagle medium; DMSO: Dimethylsulfoxide; DMSO-$d_6$: Deuterated dimethylsulfoxide; ESIMS: Electrospray ionization mass spectroscopy; HRMS: High resolution mass spectroscopy; $K_2CO_3$ Potassium carbonate; MeONa: Sodium methoxyde; $NaHCO_3$: Sodium bicarbonate; NMR: Nuclear magnetic resonance; $Na_2SO_4$: Sodium sulphate; Pd/C: Palladium on carbon; RT: Room temperature; SCID: Severe Combined Immunodeficiency; THF: Tetrahydrofuran.

Preparation of the Compounds of the Invention

The compounds of the present disclosure can be prepared according to the procedures denoted in the following reaction Schemes and Examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

As illustrated in Scheme 1, 2-(chloroseleno)benzoyl chloride is coupled with compound 12 to obtain 14. Compound 14 is then optionally deprotected to produce the hydroxyl analog 16.

Scheme 1: General synthesis of 1,2-benzisoselenazol-3(2H)-one analogs

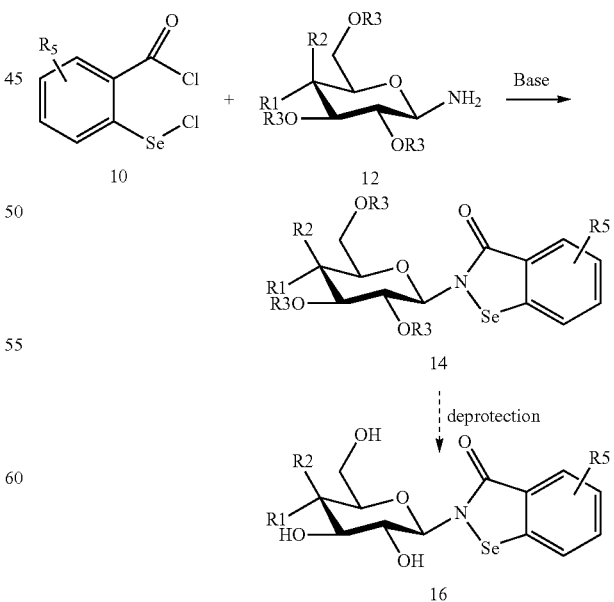

As illustrated in Scheme 2, pyranosylamine 22 and compound 20 are coupled for example by using a common peptidic coupling reagent such as DCC. The amine protecting group moiety of compound 20 is illustrated as a benzyloxycarbonyl group but other suitable protecting group can be used. The compound 24 is deprotected to produce the intermediate 26, which is then reacted with 2-(chloroseleno)benzoyl chloride to obtain compound 30. An optional deprotection of said compound 30 may result in the hydroxyl analog 32.

As illustrated in Scheme 3, the intermediate compound 34 is produced by subjecting the starting material 30 to the saccharide compound 32 in the presence of, for example, a lewis acid such as boron trifluoride. Then, the nitro moiety of compound 34 is reduced to a primary amine. Typical reduction condition comprises activated palladium on carbon. The resulting product 36 is coupled with (chloroseleno)benzoyl chloride to obtain the desired product 38, which may be reduced to form the hydroxyl analog 40. This general synthesis may be preferably employ for synthesizing compounds, wherein X is ether moiety.

Scheme 2: General synthesis of 1,2-benzisoselenazol-2(3H)-yl-amide analogs

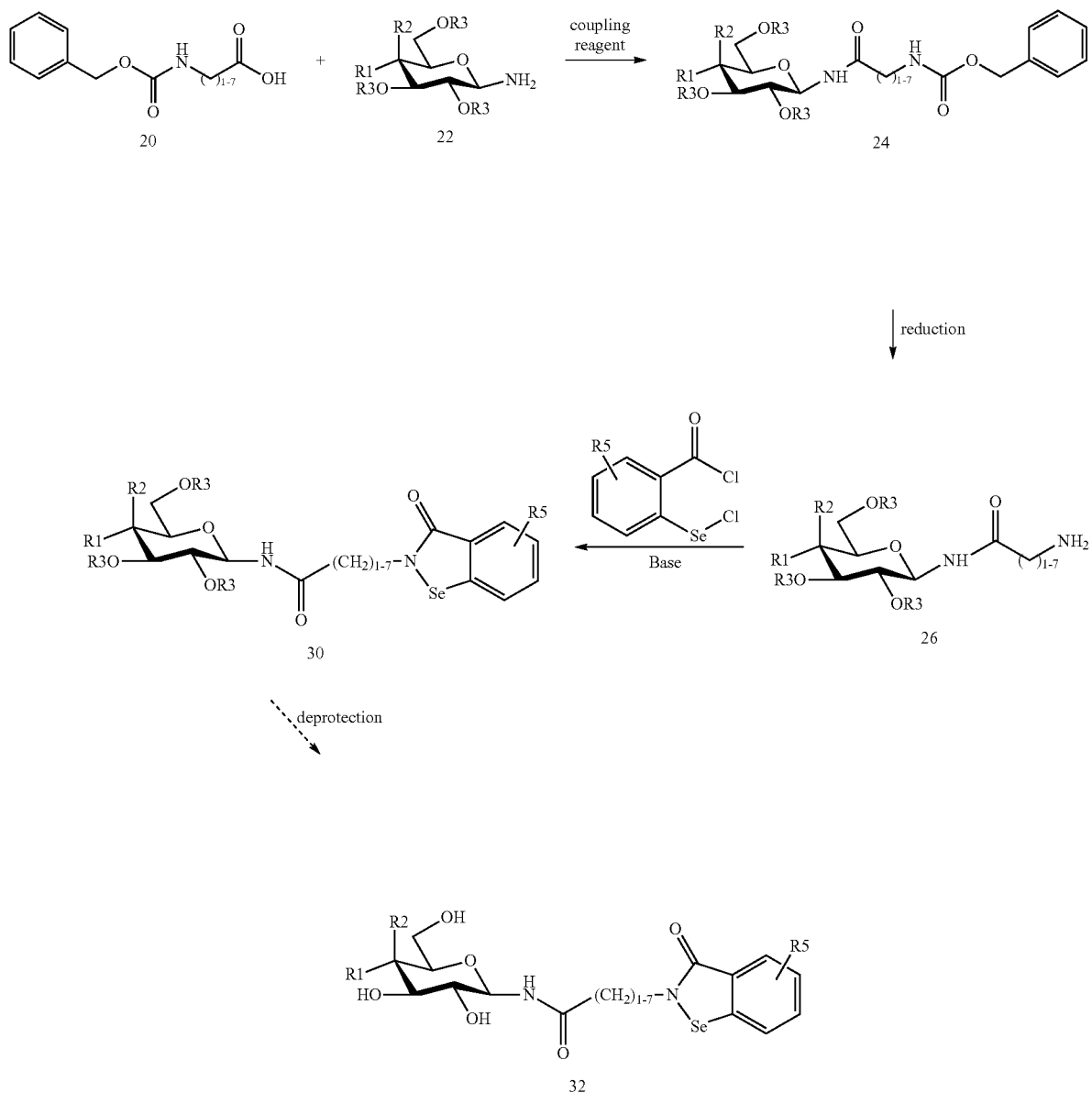

Scheme 3: General synthesis of phenzyl-(1,2)-benzisoselenazol-3(2H)-one

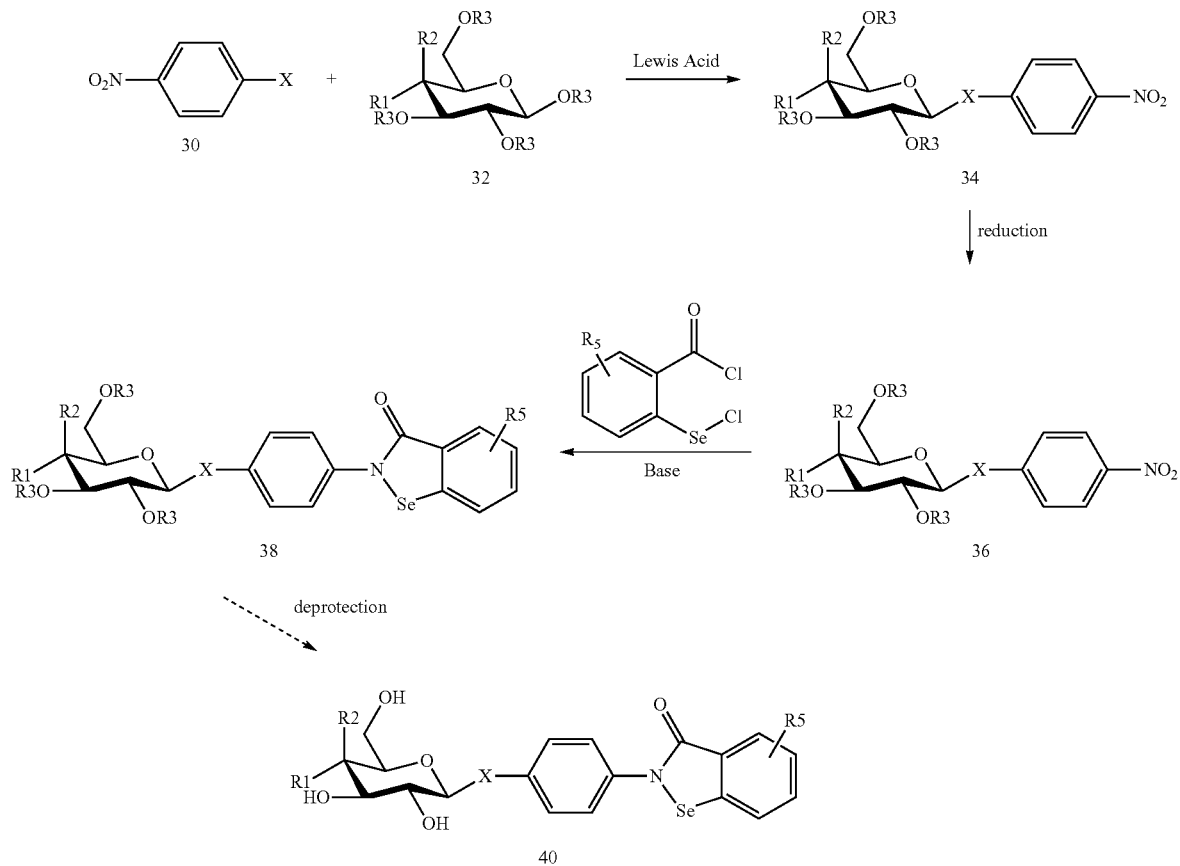

As illustrated in Scheme 4, (chloroseleno)benzoyl chloride 40 is first submitted to a basic mixture containing the amino compound 42 to obtain the intermediate 44, which is then coupled with compound 46, using for example TBAB and a base such as potassium carbonate in presence of water. The final product 48 may be deprotected using the appropriate condition depending of the protecting group used. This general synthesis may be preferably employed for synthesizing compounds, wherein X is ester moiety.

Scheme 4: General synthesis of 1,2-benzisoselenazol-2(3H)-yl-benzoate analogs

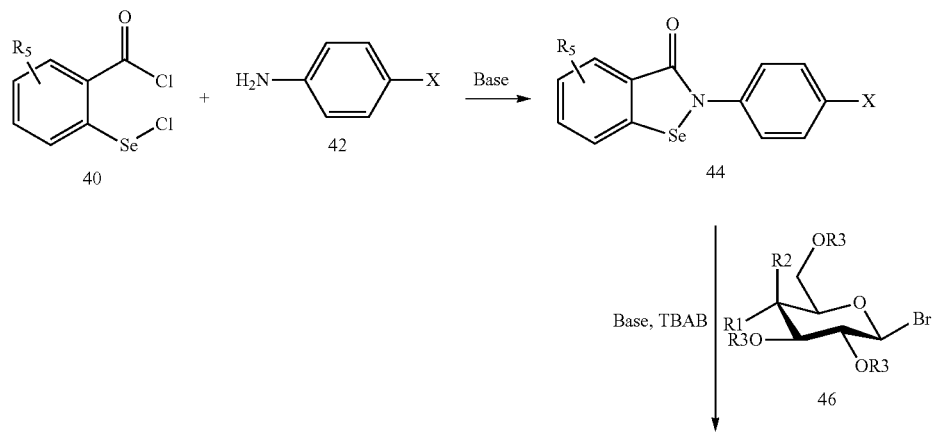

31

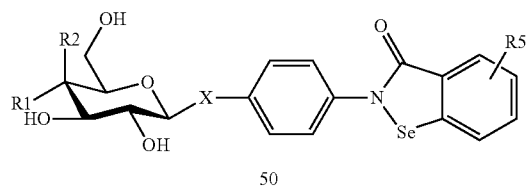

50

32

-continued

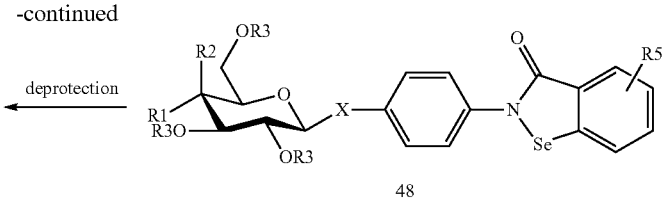

48 deprotection

The following examples are provided to further illustrate details for the preparation and use of the compounds of the present disclosure. They are not intended to be limitations on the scope of the instant invention in any way, and they should not be so construed. Furthermore, the compounds described in the following examples are not to be construed as forming the only genus that is considered as the contribution of the inventors to the art, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Example 1

2-(1-deoxy-β-D-glucopyranosyl)-1,2-benzisoselenazol-3(2H)-one

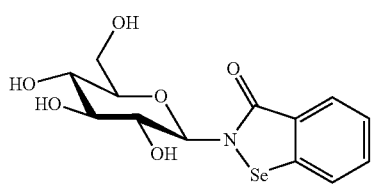

Step 1a: Synthesis of 2-(2,3,4,6-tetra-O-acetyl-1-deoxy-β-D-glucopyranosyl)-1,2-benzisoselenazol-3-(2H)-one as described in Dallacker, F. *Chemiker-Zeitung* 1991, 115.

Step 1b: Synthesis of 2-(1-deoxy-β-D-glucopyranosyl)-1,2-benzisoselenazol-3(2H)-one 2-(2,3,4,6-tetra-O-acetyl-1-deoxy-β-D-glucopyranosyl)-1,2-benzisoselenazol-3-(2H)-one (530 mg) is dissolved in 30 mL methanol. MeONa in methanol (0.63 M, 1 mL) is added at 0° C. After stirring at room temperature (RT) for 1 h, the resulting precipitate is collected and washed with methanol to produce the product (346 mg; 96%).

mp: 130-132° C.

$^1$H NMR (CD$_3$OD): δ 7.92-7.42 (m, 4H, ArH), 5.53 (d, 1H, J=8.7 Hz, C$_1$'—H), 3.86 (dd, 1H, J=2.4, 12.4 Hz, C$_6$'—H$_1$), 3.66 (dd, 1H, J=5.9, 11.9 Hz, C$_6$'—H$_2$), 3.49 (m, 3H, C$_2$'—H, C$_3$'—H, C$_5$'—H), 3.35 (m, 1H, C$_4$'—H).

$^{13}$C NMR (DMSO-d$_6$): δ 167.1, 139.8, 131.9, 128.2, 127.6, 125.8, 82.4, 79.6, 77.4, 74.3, 70.0, 61.0.

ESIMS m/z 362.0 [M+H]$^+$, 384.0 [M+Na]$^+$.

Example 2

2-(1-deoxy-2,3,4,6-tetra-O-acetyl-β-D-galactopyranosyl)-1,2-benzisoselenazol-3(2H)-one

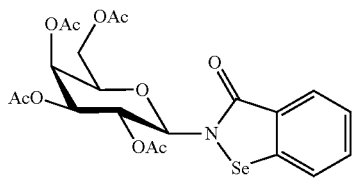

Step 2a: Synthesis of 2,3,4,6-tetra-O-acetyl-β-D-galactopyranosylamine as described in Esteves, A. *Tetrahedron* 2005, 61.

Step 2b: Synthesis of 2-(1-deoxy-2,3,4,6-tetra-O-acetyl-β-D-galactopyranosyl)-1,2-benzisoselenazol-3(2H)-one 2,3,4,6-tetra-O-acetyl-β-D-galactopyranosylamine (347 mg) is dissolved in 30 mL dry THF. A solution of 2-(chloroseleno)benzoyl chloride (254 mg) in dry THF (10 mL) and a solution of triethylamine 0.3 mL in dry THF (10 mL) are added to the mixture dropwise at the same time at 0° C. over a period of 30 min. The reaction is stirred for an additional 2 h at RT. When the reaction is completed, the crude reaction product is purified by column chromatography to afford the product as a yellow power (306 mg; 58%).

mp: 96-99° C.

$^1$H NMR (CDCl$_3$): δ 8.05-7.44 (m, 4H, ArH), 5.92 (d, 1H, J=9.1 Hz, C$_1$'—H), 5.50 (d, 1H, J=3.2 Hz C$_4$'—H), 5.35 (dd, J=9.2, 10.1 Hz 1H, C$_2$'—H), 5.22 (dd, 1H, J=3.2, 10.1 Hz, C$_3$'—H), 4.20-4.11 (m, 3H, C$_5$'—H, C$_6$'—H), 2.22-1.94 (4s, 12H, Ac—H).

$^{13}$C NMR (CDCl$_3$): δ 170.4, 170.0, 169.9, 169.5, 167.5, 138.8, 132.9, 129.0, 126.3, 126.2, 124.2, 81.2, 73.3, 71.3, 68.9, 67.1, 61.3, 20.7, 20.6, 20.5, 20.5.

MS (ESI) m/z: ES$^+$ 530.0 [M+H]$^+$, 552.0 [M+Na]$^+$.

Example 3

2-(1-deoxy-β-D-galactopyranosyl)-1,2-benzisoselenazol-3(2H)-one

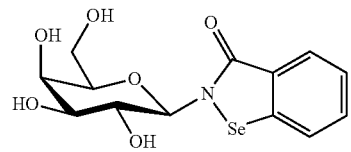

2-(1-deoxy-2,3,4,6-tetra-O-acetyl-β-D-galactopyranosyl)-1,2-benzisoselenazol-3(2H)-one (306 mg) is dissolved in 30 mL methanol. MeONa in methanol (0.63 M, 1 mL) is added at 0° C. After stirring at RT for 1 h, the resulting precipitate is collected and washed with methanol, yielding in the product (196 mg; 94%).

mp: 140-142° C.

$^1$H NMR (CD$_3$OD): δ 7.94-7.42 (m, 4H, ArH), 5.50 (d, 1H, J=8.7 Hz, C$_1$'—H), 3.95 (d, 1H, J=3.3 Hz, C$_4$'—H), 3.86 (dd, 1H, J=8.7, 9.2 Hz, C$_2$'—H), 3.78-3.72 (m, 3H, C$_6$'—H, C$_5$'—H), 3.65 (dd, 1H, J=3.3, 9.6 Hz, C$_3$'—H).

$^{13}$C NMR (DMSO-d$_6$): δ 166.9, 139.9, 131.8, 128.2, 127.5, 125.9, 125.7, 82.8, 77.8, 74.1, 71.3, 68.3, 60.6.

MS (ESI) m/z: ES$^+$ 362.0 [M+H]$^+$, 384.0 [M+Na]$^+$.

Example 4

2-(1-deoxy-2,3,6,2',3',4',6'-hepta-O-acetyl-β-D-lactosyl))-1,2-benzisoselenazol-3(2H)-one

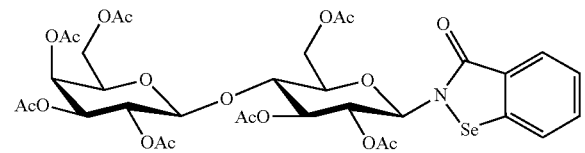

Step 4a: Synthesis of 2,3,6,2',3',4',6'-hepta-O-acetyl-β-D-lactosylamine as described in known literature processes.

Step 4b: 2,3,6,2',3',4',6'-hepta-O-acetyl-β-D-lactosylamine (635 mg) is dissolved in 30 mL dry THF. A solution of 2-(chloroseleno)benzoyl chloride (254 mg) in dry THF (10 mL) and a solution of triethylamine 0.3 mL in dry THF (10 mL) are added to the mixture dropwise at the same time at 0° C. over a period of 30 min. The reaction is stirred for an additional 2 h at RT.

When the reaction is completed, the crude reaction product is purified by column chromatography to afford the product as a yellow power (408 mg: 50%).

mp: 116-119° C.

$^1$H NMR (CDCl$_3$): δ 8.05-7.44 (m, 4H, ArH), 5.91 (d, 1H, J=8.7 Hz, C$_1$'—H), 5.39 (m, 2H, C$_3$$^1$—H, C$_4$"—H), 5.15 (m, 2H, C$_2$'—H, C$_2$"—H), 4.99 (dd, 1H, J=3.3, 10.6 Hz, C$_3$"—H), 4.53 (d, 1H, J=8.3 Hz, C$_1$"—H), 4.51 (d, 1H, J=12.4 Hz, C$_6$"—H), 4.17-4.08 (m, 3H, C$_6$'—H, C$_6$"—H), 3.91 (m, 3H, C$_4$'—H, C$_5$'—H, C$_5$"—H), 2.17-1.92 (7s, 21H, Ac—H).

$^{13}$C NMR (CDCl$_3$): δ 170.4, 170.3, 170.2, 170.1, 169.7, 169.5, 169.0, 167.6, 138.6, 132.9, 129.1, 126.4, 126.3, 124.2, 101.1, 80.6, 75.9, 75.4, 73.1, 71.7, 70.9, 70.8, 69.0, 66.6, 61.8, 60.8, 20.9, 20.8, 20.7, 20.7, 20.6, 20.5.

ESIMS m/z 818.3 [M+H]$^+$, 840.3 [M+Na]$^+$.

Example 5

2-(1-deoxy-β-D-lactosyl)-1,2-benzisoselenazol-3(2H)-one

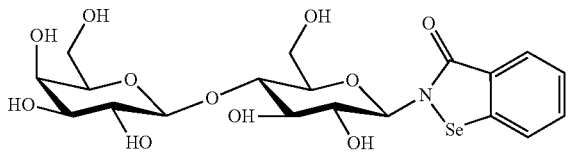

2-(1-deoxy-2,3,6,2',3',4',6'-hepta-O-acetyl-β-D-lactosyl))-1,2-benzisoselenazol-3(2H)-one (204 mg) is dissolved in 10 mL methanol. MeONa in methanol (0.63 M, 1 mL) is added at 0° C. After stirring at RT for 1 h, the resulting precipitate is collected and washed with methanol, yielding in the product which becomes dark at 180° C. (125 mg; 96%).

$^1$H NMR (CD$_3$OD): δ 7.97-7.46 (m, 4H, ArH), 5.57 (d, 1H, J=8.7 Hz, C$_1$'—H), 4.41 (d, 1H, J=7.8 Hz, C$_1$"—H), 3.93 (dd, 1H, J=2.3, 12.4 Hz, C$_6$'—H$_1$), 3.87 (dd, 1H, J=4.1, 12.4 Hz, C$_6$'—H$_2$), 3.82-3.59 (m, 8H, Lac-H), 3.59 (dd, 1H, J=7.8, 9.6 Hz, C$_2$"—H), 3.51 (dd, 1H, J=3.3, 9.6 Hz, C$_3$"—H).

$^{13}$C NMR (DMSO-d$_6$): δ 167.8, 132.6, 132.2, 131.9, 129.9, 126.1, 103.9, 80.6, 80.3, 76.7, 75.7, 75.6, 73.2, 71.6, 70.6, 68.1, 60.4, 60.3.

ESIMS m/z 524.1 [M+H]$^+$, 546.1 [M+Na]$^+$.

Example 6

2-(3-oxo-1,2-benzisoselenazol-2(3H)-yl)-N-(1-deoxy-2,3,4,6-tetra-O-acetyl-β-D-glucopyranosyl)-acetamide

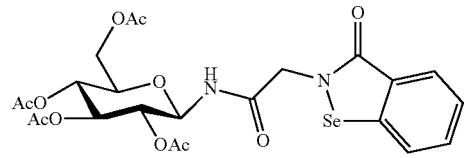

Step 6a: Synthesis of N-[2-oxo-2-[(2,3,4,6-tetra-O-acetyl-β-D-glucopyranosyl)amino]ethyl]-Carbamic phenylmethyl ester as described in Masahiko, S. *Chemical and pharmaceutical bulletin* 1984, 32.

Step 6b: Synthesis of 2-amino-N-(2,3,4,6-tetra-O-acetyl-β-D-glucopyranosyl)-acetamide as described in Masahiko, S. *Chemical and pharmaceutical bulletin* 1984, 32.

Step 6c: 2-amino-N-(2,3,4,6-tetra-O-acetyl-β-D-glucopyranosyl)-acetamide (404 mg) is dissolved in 30 mL dry THF. A solution of 2-(chloroseleno)benzoyl chloride (254 mg) in dry THF (10 mL) and a solution of triethylamine 0.3 mL in dry THF (10 mL) is added to the mixture dropwise at 0° C. over a period of 30 min. The reaction is stirred for an additional 2 h at RT. When the reaction is completed, the crude reaction product is purified by column chromatography to afford the product as a yellow power (250 mg; 42%).

mp: 97-100° C.

$^1$H NMR (CDCl$_3$): δ 8.09-7.49 (m, 4H, ArH), 7.18 (d, 1H, J=9.2 Hz, N—H), 5.28 (dd, 1H, J=9.2, 9.6 Hz, C$_1$—H), 5.24 (dd, 1H, J=9.2, 9.6 Hz, C$_3$'—H), 5.06 (dd, 1H, J=9.2, 10.1 Hz, $C_4'$—H), 4.91 (t, 1H, J=9.6 Hz, $C_2'$—H), 4.56 (d, 1H, J=16.5 Hz, —$CH_2$), 4.38 (d, 1H, J=16.9 Hz, —$CH_2$), 4.29 (dd, 1H, J=4.6, 12.4 Hz, $C_6'$—$H_1$), 4.11 (dd, 1H, J=2.3, 12.4 Hz, $C_6'$—$H_2$), 3.83 (m, 1H, $C_5'$—H), 2.08-1.89 (4s, 12H, Ac—H).

$^{13}$C NMR (CDCl$_3$): δ 170.9, 170.8, 170.1, 169.7, 168.8, 168.3, 139.1, 132.9, 129.2, 126.7, 126.1, 124.3, 78.5, 73.9, 72.9, 70.5, 68.3, 61.9, 48.4, 20.9, 20.8, 20.7, 20.6.

ESIMS m/z 587.2 [M+H]$^+$, 609.3 [M+Na]$^+$.

Example 7

2-(3-oxo-1,2-benzisoselenazol-2(3H)-yl)-N-(1-deoxy-β-D-glucopyranosyl)-acetamide

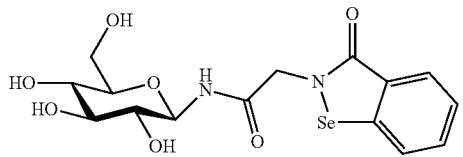

2-(3-oxo-1,2-benzisoselenazol-2(3H)-yl)-N-(1-deoxy-2,3,4,6-tetra-O-acetyl-β-D-glucopyranosyl)-acetamide (250 mg) is dissolved in 30 mL methanol. MeONa in methanol (0.63 M, 1 mL) is added at 0° C. After stirring at RT for 1 h, the resulting precipitate is collected and washed with methanol, yielding in the product which becomes dark at 169° C. (166 mg; 93%).

$^1$H NMR (DMSO-d$_6$/CD$_3$OD): δ 7.90-7.44 (m, 4H, ArH), 4.97 (d, 1H, J=9.0 Hz, $C_1'$—H), 4.16 (m, 1H, $C_4'$—H), 3.84 (dd, 1H, J=1.8, 12.0 Hz, $C_6'$—$H_1$), 3.66 (dd, 1H, J=5.4, 12.0 Hz, $C_6'$—$H_2$), 3.42 (t, 1H, J=9.0 Hz, $C_2'$—H), 3.35 (m, 2H, $C_3'$—H, $C_5'$—H).

$^{13}$C NMR (DMSO-d$_6$): δ 168.9, 168.1, 132.8, 132.5, 128.1, 126.9, 126.1, 80.3, 79.4, 77.9, 72.8, 70.5, 61.4, 56.3.

MS (ESI) m/z: ES$^+$ 419.0 [M+H]$^+$

Example 8

2-(4-(2,3,4,6-tetra-O-acetyl-β-D-glucopyranosyl) phenzyl)-1,2-benzisoselenazol-3(2H)-one

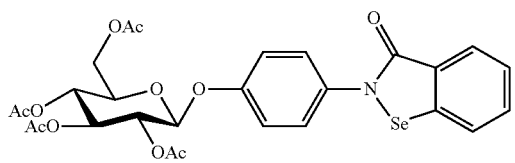

Step 8a: Synthesis of 1-(4-nitrophenyl)-2,3,4,6-tetra-O-acetyl-β-D-glucopyranoside as described in Soo, L. Y. *Journal of carbohydrate chemistry* 2001, 20.

Step 8b: Synthesis of 1-(4-aminophenyl)-2,3,4,6-tetra-O-acetyl-β-D-glucopyranoside as described in Winum, J.-Y. *Farmaco* 2001, 56.

Step 8c: 1-(4-aminophenyl)-2,3,4,6-tetra-O-acetyl-β-D-glucopyranoside (440 mg) is dissolved in 30 mL dry THF. A solution of 2-(chloroseleno)benzoyl chloride (254 mg) in dry THF (10 mL) and a solution of triethylamine 0.3 mL in dry THF (10 mL) are added dropwise at 0° C. over a period of 30 min. And the reaction is stirred for an additional 2 h at RT. When the reaction is completed, the crude reaction product is purified by column chromatography to afford the product as yellow power (248 mg; 40%).

mp: 143-144° C.

$^1$H NMR (CDCl$_3$): δ 8.12-7.07 (m, 8H, ArH), 5.33 (m, 2H, $C_2'$—H, $C_4'$—H), 5.12 (t, 1H, J=9.1 Hz, $C_3'$—H), 5.10 (d, 1H, J=7.3 Hz, $C_1'$—H), 4.32 (dd, 1H, J=5.5, 12.4 Hz, $C_6'$-$H_1$), 4.19 (dd, 1H, J 2.4, 12.4 Hz, $C_6'$—$H_2$), 3.89 (m, 1H, $C_5'$—H), 2.09-2.05 (4s, 12H, Ac—H).

$^{13}$C NMR (CDCl$_3$): δ 170.6, 170.2, 169.4, 169.3, 165.9, 155.3, 137.7, 134.1, 132.5, 129.3, 127.2, 127.1, 126.6, 123.8, 117.7, 99.2, 72.6, 72.1, 71.1, 68.2, 61.9, 20.7, 20.6, 20.5, 20.5.

MS (ESI) m/z: ES$^+$ 622.0 [M+H]$^+$, 644.1 [M+Na]$^+$.

Example 9

2-(4-(β-D-glucopyranosyl)phenzyl)-1,2-benzisoselenazol-3(2H)-one

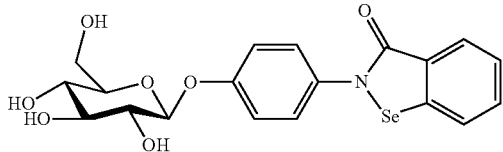

2-(4-(2,3,4,6-tetra-O-acetyl-β-D-glucopyranosyl)phenzyl)-1,2-benzisoselenazol-3(2H)-one (248 mg) is dissolved in 20 mL methanol. MeONa in methanol (0.63 M, 1 mL) was added at 0° C. After stirring at RT for 1 h, the resulting precipitate is collected and washed with methanol, yielding in the product which becomes dark at 165° C. (178 mg; 98%).

$^1$H NMR (CD$_3$OD): δ 7.99-7.21 (m, 8H, ArH), 4.96 (d, 1H, J=7.3 Hz, $C_1'$—H), 3.91 (dd, 1H, J=2.3, 11.9 Hz, $C_6'$—$H_1$), 3.72 (dd, 1H, J=6.0, 11.9 Hz, $C_6'$—$H_2$), 3.48 (m, 3H, $C_2'$—H, $C_3'$—H, $C_5'$—H), 3.41 (m, 1H, $C_4'$—H).

$^{13}$C NMR (DMSO-d$_6$): δ 164.9, 155.3, 139.2, 133.6, 131.9, 128.6, 127.8, 126.2, 126.1, 126.0, 116.8, 100.6, 77.1, 76.6, 73.2, 69.7, 60.7.

MS (ESI) m/z: ES$^+$ 453.9 [M+H]$^+$, 475.9 [M+Na]$^+$.

Example 10

(2,3,4,6-tetra-O-acetyl-β-D-glucopyranosyl)-4-(3-oxo-1,2-benzisoselenazol-2(3H)-yl)benzoate

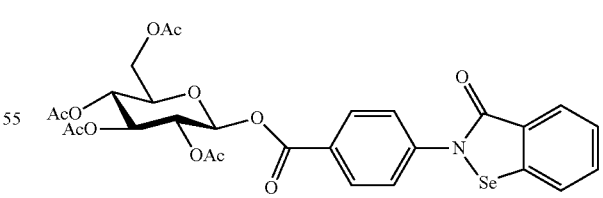

Step 10a: Synthesis of 4-(1,2-benzisoselenazol-3-(2H)-one-2-yl)benzonic acid as described in Yu, L. *Helvetica Chimica Acta* 2002, 85.

Step 10b: Synthesis of the glycosyl donor, 2,3,4,6-tetra-O-acetyl-α-D-glucopyranosyl bromide as described in Setsuo, S. *Chemical and pharmaceutical bulletin* 1985, 33.

Step 10c: To a solution of water (5 mL) and chloroform (5 mL) is added tetrabutyl ammonium bromide (320 mg). A mixture of 4-(1,2-benzisoselenazol-3-(2H)-one-2-yl)benzonic acid (320 mg) and K$_2$CO$_3$ (414 mg) in water (20 mL) is added. Then the solution of glucose donor 2,3,4,6-tetra-O-acetyl-α-D-glucopyranosyl bromide (615 mg) in chloroform (20 mL) is added dropwise at room temperature to the mixture. After 6 h of stirring, the organic layer is separated and washed successively with water, aq NaHCO$_3$, and water, dried over Na$_2$SO$_4$, and concentrated under reduced pressure. The crude reaction product is purified by column chromatography to afford the product (260 mg; 40.5%).

mp. 215-218° C.

$^1$H NMR (CDCl$_3$) δ: 7.48-8.13 (m, 8H, ArH), 5.95 (m, 1H, C$_1$'—H), 5.19-5.36 (m, 3H C$_2$'—H☐C$_3$'—H, C$_4$'—H), 4.35 (dd, 1H, J=4.44, 12.48 Hz, C$_6$'—H$_1$), 4.16 (dd, 1H, J=2.16, 12.78 Hz, C$_6$'—H$_2$), 3.94-3.97 (m, 1H, C$_5$'—H), 2.01-2.09 (4s, 12H, Ac—H).

$^{13}$C NMR (CDCl$_3$) δ: 170.6, 170.1, 169.4, 169.3, 165.8, 163.7, 144.7, 137.0, 133.1, 131.5, 129.6, 127.4, 126.8, 125.4, 123.9, 123.7, 92.3, 72.8, 72.6, 70.1, 67.9, 61.4, 20.7, 20.6.

MS (ESI) m/z: ES$^+$ 650.0 [M+H]$^+$.

Example 11

(2,3,6,2',3',4',6'-hepta-O-acetyl-β-D-lactosyl)-4-(3-oxo-1,2-benzisoselenazol-2(3H)-yl)benzoate

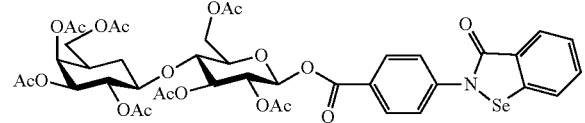

Step 11a: Synthesis of 4-(1,2-benzisoselenazol-3-(2H)-one-2-yl)benzoic acid as described in Yu, L. *Helvetica Chimica Acta* 2002, 85.

Step 11b: Synthesis of lactose donor 2,3,6,2',3',4',6'-hepta-O-acetyl-α-D-lactosyl bromide as described in the chemical literature Step 11c: To a solution of water (5 mL) and chloroform (5 mL) is added tetrabutyl ammonium bromide (320 mg). A mixture of 4-(1,2-benzisoselenazol-3-(2H)-one-2-yl)benzonic acid (320 mg) and K$_2$CO$_3$ (414 mg) in water (20 mL) is added to the first solution. Then a solution of lactose donor 2,3,6,2',3',4',6'-hepta-O-acetyl-α-D-lactosyl bromide (1.04 g) in chloroform (20 mL) is added dropwise at RT to the mixture. After 6 h of stirring, the organic layer is separated and washed successively with water, aq NaHCO$_3$, and water, dried over Na$_2$SO$_4$, and concentrated under reduced pressure. The crude product is purified by column chromatography to afford the product (360 mg, 40.8%).

mp 141-143° C.

$^1$H NMR (CDCl$_3$) δ: 7.67-8.13 (m, 8H, ArH), 5.90 (d, 1H, J=8.22 Hz, C$_1$'—H) 5.36 (m, 1H, C$_4$'—H), 5.34 (d, 1H, J=8.70 Hz, C$_1$''—H) 5.27 (dd, 1H, J=8.22, 9.18 Hz, C$_2$'—H), 5.14 (dd, 1H, J=7.80, 10.08 Hz C$_2$''—H), 4.96 (dd, 1H, J=3.24, 9.96 Hz, C$_3$''—H), 4.50 (d, 1H, J=7.80 Hz, C$_4$''—H), 4.48 (dd, 1H, J=1.86, 11.96 Hz, C$_6$''—H$_1$), 4.14-4.18 (m, 2H, C$_6$''—H$_2$, C$_3$'—H), 4.10 (dd, 1H, J=7.32, 10.98 Hz, C$_6$'—H$_1$), 3.86-3.94 (m, 3H, C$_6$'—H$_2$, C$_5$'—H, C$_5$''—H), 2.17-1.97 (7s, 21H, Ac—H).

$^{13}$C NMR (CDCl$_3$)$_6$: 170.4, 170.3, 170.1, 170.0, 169.6, 169.5, 169.0, 165.8, 163.6, 144.6, 136.9, 133.1, 131.4, 129.5, 127.4, 126.8, 125.5, 123.9, 123.6, 100.9, 92.2, 75.7, 73.5, 72.4, 70.9, 70.7, 70.4, 68.9, 66.6, 61.7, 60.8, 20.8, 20.7, 20.6, 20.5.

MS (ESI): ES$^+$ 938.2 [M+H]$^+$.

Example 12

4-(3-oxo-1,2-benzisoselenazol-2(3H)-yl)-N-(1-deoxy-2,3,4,6-tetra-O-acetyl-β-D-glucopyranosyl)-butyramide

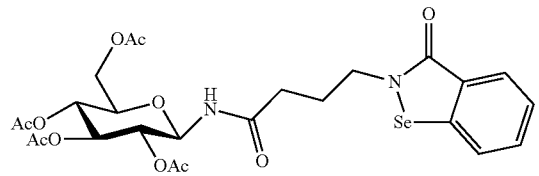

Step 12a: Synthesis of 2,3,4,6-tetra-O-acetyl-β-D-glucopyranosylamine as described in Esteves, A. *Tetrahedron* 2005, 61.

Step 12b: Synthesis of N-[4-oxo-4-[(2,3,4,6-tetra-O-acetyl-β-D-glucopyranosyl)amino]butyl]-carbamic phenylmethyl ester 2,3,4,6-tetra-O-acetyl-β-D-glucopyranosylamine (694 mg) and 4-(benzyloxycarbonyl)butanoic acid (480 mg) are dissolved in 30 mL dry CH$_2$Cl$_2$. DCC (430 mg) is added to the mixture in portion at 0° C. The reaction is stirred for an additional 5 h at RT. The mixture is then filtered and the organic layer is washed successively with water, aq NaHCO$_3$, and water, dried over Na$_2$SO$_4$. Once the resulting mixture is filtered, the organic layer is concentrated under reduced pressure to afford the product (1.02 g; 90%).

Step 12c: Synthesis of 4-amino-N-(2,3,4,6-tetra-O-acetyl-β-D-glucopyranosyl)-butyramide Pd/C (10%) is added to a solution of N-[4-oxo-4-[(2,3,4,6-tetra-O-acetyl-β-D-glucopyranosyl)amino]butyl]-carbamic phenylmethyl ester (1.02 g) in 30 mL methanol/THF (1:1). The reaction mixture is stirred under hydrogen at room temperature for 5 h. The mixture is filtered through diatomite and is concentrated to give the product (760 mg; 98%).

Step 12d: Synthesis of 4-(3-oxo-1,2-benzisoselenazol-2 (3H)-yl)-N-(1-deoxy-2,3,4,6-tetra-O-acetyl-β-D-glucopyranosyl)-butyramide 4-amino-N-(2,3,4,6-tetra-O-acetyl-β-D-glucopyranosyl)-butyramide (432 mg) is dissolved in 30 mL dry THF. A solution of 2-(chloroseleno)benzoyl chloride (254 mg) in dry THF (10 mL) and a solution of triethylamine 0.3 mL in dry THF (10 mL) are added to the mixture dropwise at 0° C. over a period of 30 min. The reaction is stirred for an additional 2 h at room temperature. When the reaction is completed, the crude reaction product is purified by column chromatography to afford the product as a yellow power (295 mg; 48%).

mp: 82-86° C.

$^1$H NMR (CDCl$_3$): δ 8.05-7.43 (m, 4H, ArH), 6.99 (d, 1H, J=9.2 Hz, N—H), 5.27 (m, 2H, C$_3$'—H, C$_4$'—H), 5.07 (m, 1H C$_2$'—H), 4.97 (m, 1H, C$_1$'—H), 4.27 (dd, 1H, J=4.6, 12.4 Hz, C$_6$'—H$_1$), 4.08 (dd, 1H, J=2.3, 12.4 Hz, C$_6$'—H$_2$), 3.92 (m, 1H, C$_5$'—H), 3.80 (m, 2H, α-CH$_2$), 2.24 (m, 2H, γ-CH$_2$), 2.01-2.08 (4s, 12H, Ac—H), 1.77 (m, 2H, β-CH$_2$).

$^{13}$C NMR (CDCl$_3$): δ 172.7, 170.7, 170.0, 169.6, 167.7, 137.8, 132.3, 129.1, 127.1, 126.4, 124.1, 78.2, 73.6, 73.1, 70.7, 68.2, 61.7, 43.7, 33.0, 26.2, 20.8, 20.8, 20.7.

ESIMS m/z 615.1 [M+H]$^+$, 637.1[M+Na]$^+$.

Example 13

4-(3-oxo-1,2-benzisoselenazol-2(3H)-yl)-N-(1-deoxy-β-D-glucopyranosyl)-butyramide

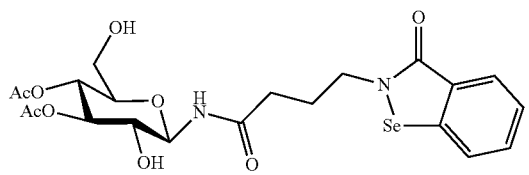

4-(3-oxo-1,2-benzisoselenazol-2(3H)-yl)-N-(1-deoxy-2,3,4,6-tetra-O-acetyl-β-D-glucopyranosyl)-butyramide (250 mg) is dissolved in 30 mL methanol. MeONa in methanol (0.63 M, 1 mL) is added at 0° C. After stirring at RT for 1 h, the resulting precipitate is collected and washed with methanol, yielding to the product (171 mg; 94%).

mp: 189-191° C.

$^1$H NMR (DMSO-d$_6$): δ 8.39 (d, 1H, J=9.4 Hz, N—H), 8.05-7.40 (m, 4H, ArH), 4.96 (d, 1H, J=5.0 Hz, —OH), 4.86 (d, 1H, J=6.0 Hz, —OH)-4.85 (d, 1H, J=5.4 Hz, —OH), 4.69 (dd, 1H, J=8.8, 9.3 Hz, C$_1$'—H), 4.47 (dd, 1H, J=5.4, 6.1 Hz, —OH), 3.68 (m, 2H, α-CH$_2$), 3.61-3.00 (m, 6H, Glu-H)-2.12 (m, 2H, γ-CH$_2$), 1.80 (m, 2H, β-CH$_2$).

$^{13}$C NMR (DMSO-d$_6$): δ 171.9, 166.4, 139.2, 131.4, 128.0, 127.3, 125.8, 125.7, 79.5, 78.5, 77.5, 72.5, 69.9, 42.8, 32.3, 25.8.

ESIMS m/z 447.1 [M+H]$^+$, 469.1[M+Na]$^+$.

Example 14

Inhibition of Cell Proliferation

Exponentially growing DU145 or MDA-231 cells (1×10$^3$ cells) were seeded in 96-well plates. After 18 hours cells were continuously treated with compound listed in Table 1 dissolved in DMSO. The final concentration of DMSO was less than 0.05%. After 96 hours, the cell survival was evaluated using 3-(4,5-dimethylthiazo-2-yl)-2,5-diphenyltetrazolium bromide (MTT) metabolic assay. The inhibitory activity (IC$_{50}$) of the compounds on MDA-231 and DU145 cell proliferation was determined. The results are presented in Table 1 for a representative number of compounds.

Example 15

In Vitro Kinase Activity

Human recombinant full-length kinases were incubated in kinase buffer containing ATP and substrate (Poly Glu:Tyr) for 4 hours at room temperature with or without the presence of the compounds listed in Table 1 at various concentrations. Remaining ATP in solution was then quantified using the Kinase-Glo-luminescence™ kit (Promega). The percentage of inhibition of the tested compounds to inhibit focal adhesion kinase activity is presented in Table 1. Results regarding other kinases for compounds described herein are presented in Table 2.

TABLE 1

Inhibition of cell proliferation and FAK kinase activity for various compounds.

| Compound No. | MDA231- IC$_{50}$ (μM) | DU145- IC$_{50}$ (μM) | FAK inhibition (% at 1 μM) |
|---|---|---|---|
| 1 | 9.8 | 14.6 | 80.1 |
| 2 | >100 | 224.0 | 1.3 |
| 3 | 21.0 | 24.3 | 69.3 |
| 4 | >100 | 220.0 | 7.4 |
| 5 | 18.1 | 24.6 | 54 |
| 6 | 275.0 | 145.0 | 9 |
| 7 | 52.0 | 40.3 | 8 |
| 8 | 24.6 | 33.7 | 12 |
| 9 | 380.0 | 277.0 | 4 |
| 10 | 57.5 | 30.6 | 11 |
| 11 | 28.5 | 57.3 | 17 |
| 12 | 20.4 | 18.4 | 51.9 |
| 13 | 18.9 | 12.3 | 71.1 |
| 14 | 54.0 | 66.4 | 13 |
| 15 | 25 | 34.5 | 55.9 |
| 16 | 53 | 39.7 | 13.9 |
| 17 | 35 | 30.4 | 51.9 |
| 18 | >100 | 125.0 | 50.9 |
| 19 | 5.2 | 11.9 | 55 |
| 20 | 550.0 | 395.0 | 15 |
| 21 | 5.5 | — | 54 |
| 22 | 2.7 | — | 60 |
| 23 | 12.7 | — | 32 |
| 24 | 15.3 | — | 72 |
| 25 | 11.4 | — | 65 |
| 26 | 4.4 | — | 15 |
| 27 | 6.8 | — | 12 |
| 28 | 4.3 | — | 85 |
| 29 | 3.7 | — | 11 |
| 30 | 2.2 | — | 94 |
| 31 | 22.9 | — | 8 |

TABLE 2

Kinase profiling for compounds 1, 12, 13 and Ebselen (all at tested at 1 μM).

| Kinase | Compound 1 % Inhibition; IC$_{50}$ [μM] | Compound 12 % Inhibition; IC$_{50}$ [μM] | Compound 13 % Inhibition; IC$_{50}$ [μM] | Ebselen % Inhibition |
|---|---|---|---|---|
| AKT-1 | 63; 0.83 | 67; 0.80 | 60; 0.88 | 22 |
| FAK | 89; 0.42 | 69; 0.92 | 55; 0.96 | 1 |
| PKC-α | 95; 0.22 | 77; 0.74 | 74; 0.73 | 25 |
| IGF1R | 0 | 0 | 0 | 0 |
| ABL1 | 0 | 0 | 0 | 0 |
| Aurora A | 0 | 0 | 0 | 0 |
| Aurora B | 0 | 0 | 0 | 0 |
| CDK1/Cyclin B | 0 | 0 | 0 | 0 |
| DDR1 | 0 | 0 | 0 | 0 |
| EGFR | 0 | 0 | 0 | 0 |
| EPHA1 | 0 | 0 | 0 | 0 |
| FGFR1 | 0 | 0 | 0 | 0 |
| FLT3 | 0 | 0 | 0 | 0 |
| FYN | 0 | 0 | 0 | 0 |
| HER2 | 0 | 0 | 0 | 0 |
| IKK-ε | 0 | 0 | 0 | 0 |
| INSR | 0 | 0 | 0 | 0 |
| LYN | 0 | 0 | 0 | 0 |
| MET | 0 | 0 | 0 | 0 |
| P38-γ | 0 | 0 | 0 | 0 |
| PAK1 | 0 | 0 | 0 | 0 |
| PDGFR-β | 0 | 0 | 0 | 0 |
| PIM1 | 0 | 0 | 0 | 0 |
| PLK4 | 0 | 0 | 0 | 0 |
| RPS6KA4 | 0 | 0 | 0 | 0 |
| SGK3 | 0 | 0 | 0 | 0 |
| SRC | 0 | 0 | 0 | 0 |
| SYK | 0 | 0 | 0 | 0 |
| TIE1 | 0 | 0 | 0 | 0 |

TABLE 2-continued

Kinase profiling for compounds 1, 12, 13 and Ebselen (all at tested at 1 μM).

| Kinase | Compound 1 % Inhibition; IC$_{50}$ [μM] | Compound 12 % Inhibition; IC$_{50}$ [μM] | Compound 13 % Inhibition; IC$_{50}$ [μM] | Ebselen % Inhibition |
|---|---|---|---|---|
| TRKB | 0 | 0 | 0 | 0 |
| VEGFR2 | 0 | 0 | 0 | 0 |
| YES1 | 0 | 0 | 0 | 0 |

Example 16

Cellular FAK Kinase Assay

MDA231 cells were serum starved overnight, treated with each compound for 2 hrs and then stimulated with 20 ng/ml EGF. Control without EGF and no treatment was included to confirm FAK activation. After 30 min, cells were washed with cold PBS and then lysed in a lysis buffer (50 mM HEPES; 150 mM NaCL; 10 mM MgCl2; 0.5 mM EGTA; 0.1% Triton X-100; 10% glycerol; 0.5 mM DTT; 1 mM Na3VO4; 1 mM PMSF; 5 mg/ml aprotinin; and 5 mg/ml leupeptin) and immunoprecipitated with a polyclonal anti-FAK antibody (C-20; Santa Cruz Biotechnologies). The resulting immunocomplex was used for FAK kinase assay using a kinase buffer (10% glycerol, 20 mM Hepes, 10 mM MgCl2, 10 mM MnCl2, and 100 mM NaCl) containing 3 μCi/nmol [γ-32P]-ATP (4500 Ci/mmol). Reactions were stopped with SDS-PAGE sample buffer and boiling for 5 min. Samples were resolved by SDS-PAGE electrophoresis and excised bands were used to quantify the radioactivity using scintillation counting.

Figure 1B:
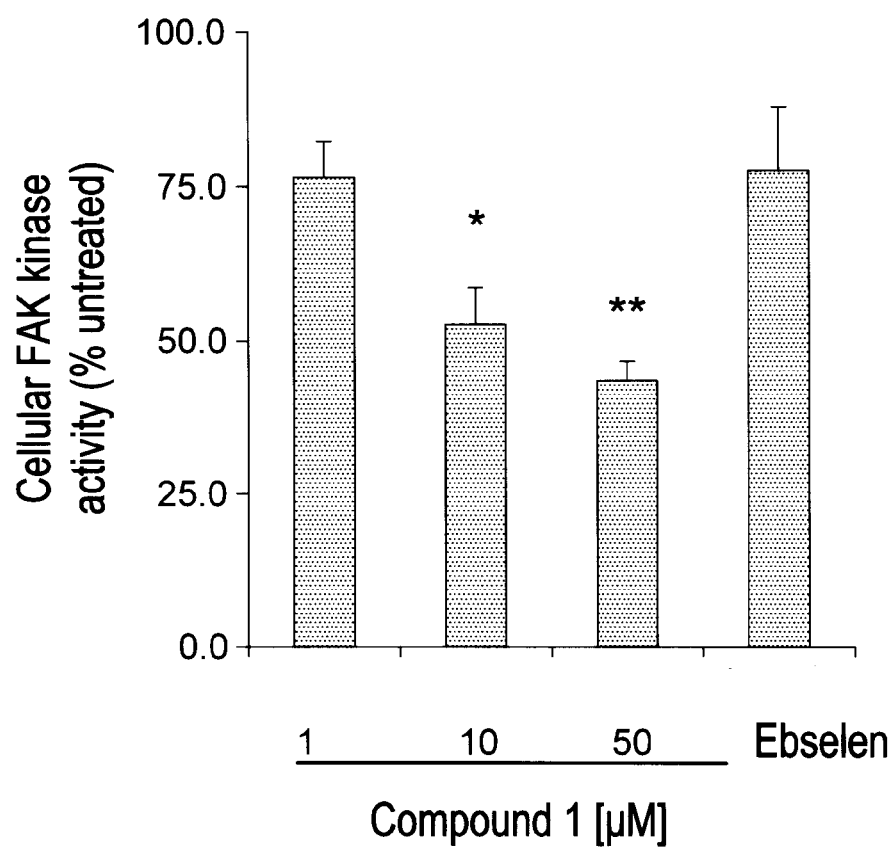

The cellular inhibitory activity of compound 1 was demonstrated on FAK phosphorylation at the critical phospho-site Y397 (FIG. 1A) and FAK kinase activity in intact cells (FIG. 1B). As noted, a concentration of 10 μM was able to inhibit FAK phosphorylation (FIG. 1A), whereas inhibition of FAK kinase activity was obtained at 10-50 μM (FIG. 1B). Higher concentrations were found to be toxic to the cells. To rule-out potential "off target" effects of the compound, in vitro studies have been conducted revealed that the compound 1, 12 and 13 (with inhibitory activity against FAK, AKT-1 and PKC-α) had no significant activity on lipooxygenase (using Lipoxygenase Screening Assay Kit, Cayman Chemical), nor do they inhibit free radical formation (using the CM-H2DCFDA-based assay for the detection of reactive oxygen species) (data not shown).

Example 17

Cell Motility and Cell Invasion

Figure 2:
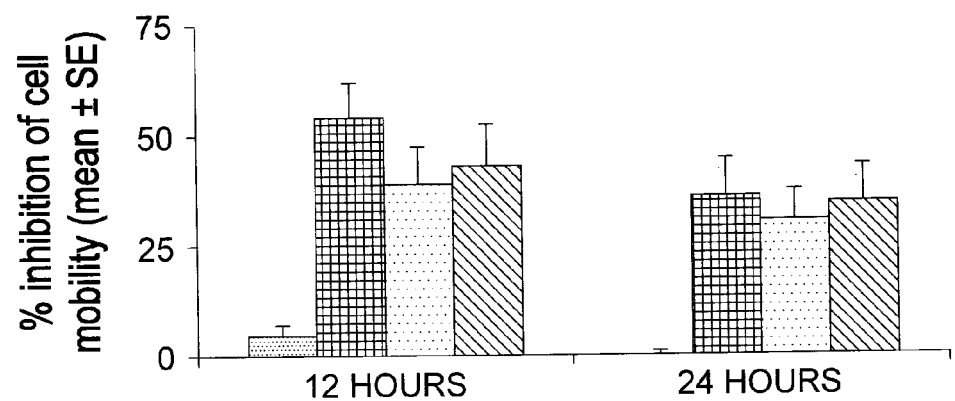
FIG. 2 provides an histogram comparing the inhibition of cell migration (% with respect to control untreated cells) of ebselen and compounds of the present disclosure after 12 and 24 hours. Cell migration was analyzed by the wound healing assay. MDA-231 cells treated with ebselen ( ) at 50 μM or compounds 1 (⊞), 12 ( ) or 13 (◊) at 10 μM, were wounded and monitored for 12 and 24 h to determine the rate of migration into the scratched area. Results are provided as percentage of inhibition of cell migration (with respect to control untreated cells) in function of time (12 or 24 hours). Bar graph represents the mean±SD of five independent experiments.

The effect of some of the compounds listed above on cell motility was investigated using the wound healing motility assay. In this study, cells were grown on sterile cover slips for 24 h and were then wounded by cell scraping using a micropipette tip. Cultures were washed and then incubated with fresh culture media at 37° C. with or without the presence of ebselen or compounds described for the indicated time periods. Cells were allowed to migrate and heal the wound. Photomicrographs were taken at each time point in order to examine the wound healing areas. The inhibitory activity of compounds on MDA-231 cell motility is demonstrated in FIG. 2. Similar results were obtained with DU145 cells (data not shown).

Figure 3:
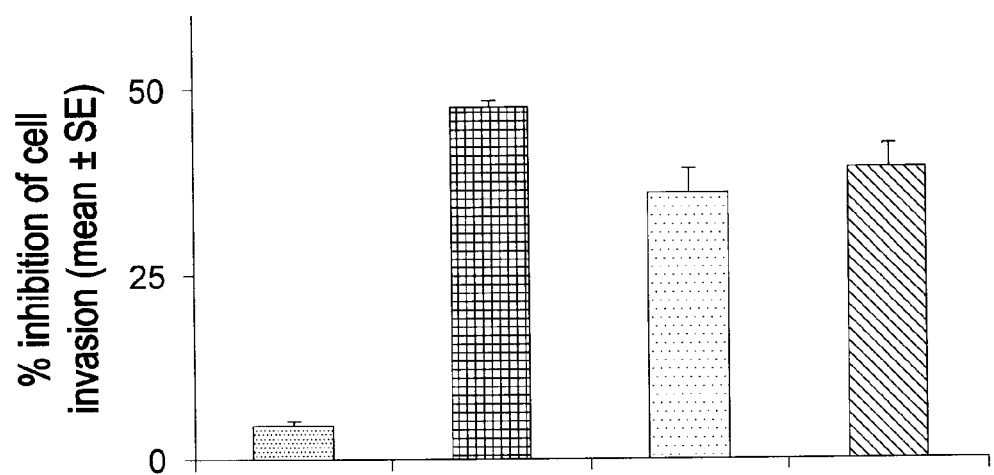
FIG. 3 provides an histogram comparing the inhibition of cell invasion (% with respect to control untreated cells) of ebselen and compounds of the present disclosure. Cell invasion was analyzed with the Boyden chamber assay. MDA-231 cells treated were treated with ebselen ( ) at 50 μM or compounds 1 (⊞), 12 ( ) or 13 (◊) at 10 μM was analyzed using as described herein. Results are shown as the percentage of inhibition of cell invasion (with respect to control untreated cells) calculated from the mean number of invaded cells. Results are expressed as the mean±SD of five independent experiments and five fields per condition.

Cell invasion experiments were performed with 8-nm porous chambers coated with Matrigel™ (Becton Dickinson). Serum starved cells were placed into the upper compartment (30 000 cells) of the Boyden chamber with or without the tested compounds and the chambers were then placed into 24-well culture dishes containing 4000 of DMEM 0.2% BSA with 10% serum (lower compartment). Cells were allowed to invade through the Matrigel™ membrane for 48 h. The invasive cells underneath the membrane were fixed and stained. Filters were viewed under bright-field 40× objective and the counting was performed for three fields in each sample. The ability of the tested compounds to inhibit MDA-231 invasiveness is demonstrated in FIG. 3. Similar results were obtained in DU145 cells (data not shown).

Example 18

In Vivo Tumorigenicity and Invasion Studies in Mice

Figure 4A:
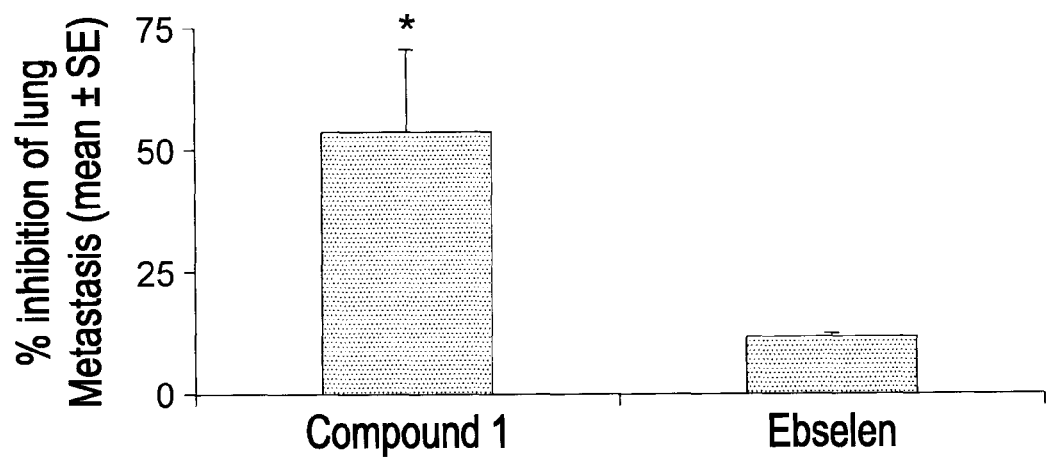
FIG. 4 provides an histogram comparing the inhibition of in vivo lung metastasis (% with respect to control vehicle treated animals) of ebselen and a compound of the present disclosure. MDA-231-M2 cells were implanted into the mammary fat pad of 6 SCID mice per condition as described herein. Once the tumor became palpable, mice were treated with vehicle, compound 1 or ebselen) at 60 mg/kg IP for a total of 9 injections. Mice were then subjected to autopsy and lung metastases and primary tumor volume were examined. Panel A) show the mean number of lung metastases±SEM (*, P<0.01) (left panel), and panel B) the primary tumor volume as weight±SEM (*, P<0.01), as compared to vehicle controls. Bottom panel shows representative lungs with metastatic nodules. Results were obtained from five mouse for each compound used.
Figure 4B:
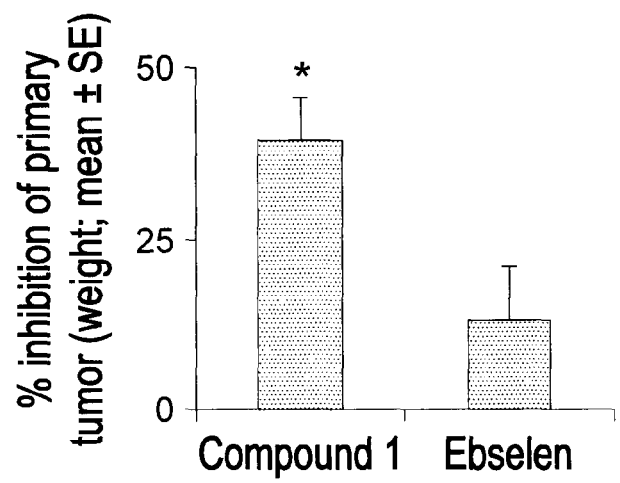

The ability of these compounds to inhibit breast cancer cell metastasis is investigated in a highly invasive mouse model of human breast cancer in vivo. In vivo studies were conducted in accordance with institutional and Canadian Federal Guidelines. Female SCID mice were obtained from Charles River Laboratories, St. Zotique, QC, Canada. Briefly, 1.5 million MDA-231-M2 cells, a highly invasive human breast cancer cell line, were injected into the mammary fat pad of female SCID mice. Once a palpable tumor was observed, animals were treated with vehicle, compound 1 or ebselen 3-4 times a week (60 mg/kg IP, 9 total injections). Animals were sacrificed on day 40, lungs were fixed in 10% Bouin's fixative, and lung surface metastases were counted using a stereomicroscope. As demonstrated in FIGS. 4 and 5, treatment with compound 1 resulted in a significant inhibition of lung surface metastases and primary tumor volume, as compared to vehicle or ebselen treated animals.

The invention claimed is:

1. A compound of formula I:

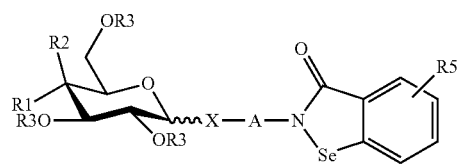

or a pharmaceutically acceptable salt or solvate thereof, wherein

X is —O—, —OCO—, —NR10CO—, or absent;
A is arylene, C1-7 alkylene or a bond;
R10 is H or C1-3 alkyl;
R1 and R2 are each independently H, OR3 or a moiety selected from the following structures:

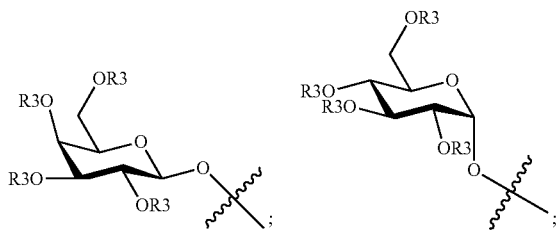

-continued

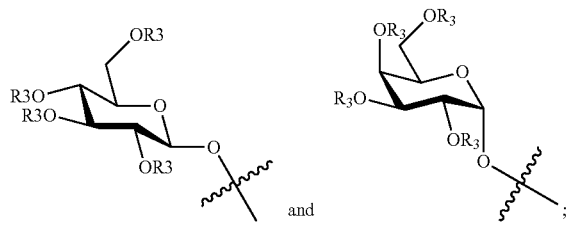
and

R3 are each independently H or a protecting group;
provided that one of R1 or R2 is H;
R5 is one or more optional substituent; and
provided that when said compound of formula I has the formula II

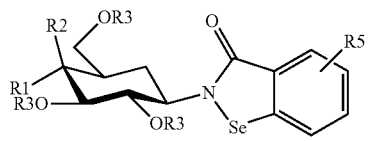

II

R3 is a protecting group that is an acetyl group and R5 is absent, then one of said R1 or R2 is H and the other of said R1 or R2 is a moiety selected from the following structures:

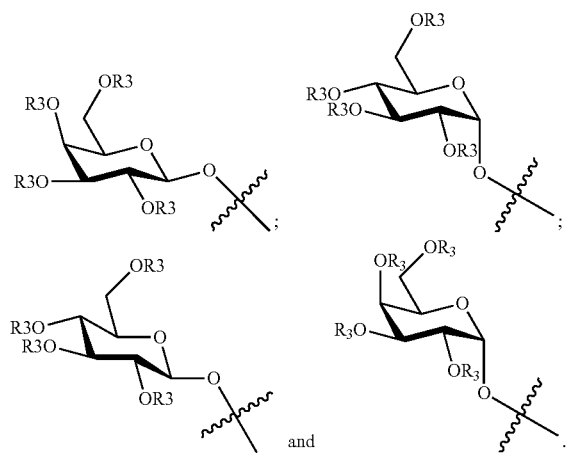
and

2. The compound of claim 1, or a pharmaceutically acceptable salt or solvate thereof, wherein said compound of formula II:

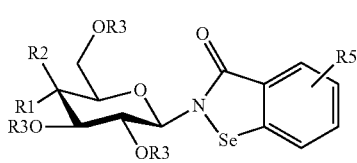

II wherein one of R1 or R2 is H and the remaining of R1 is a moiety selected from the following structures:

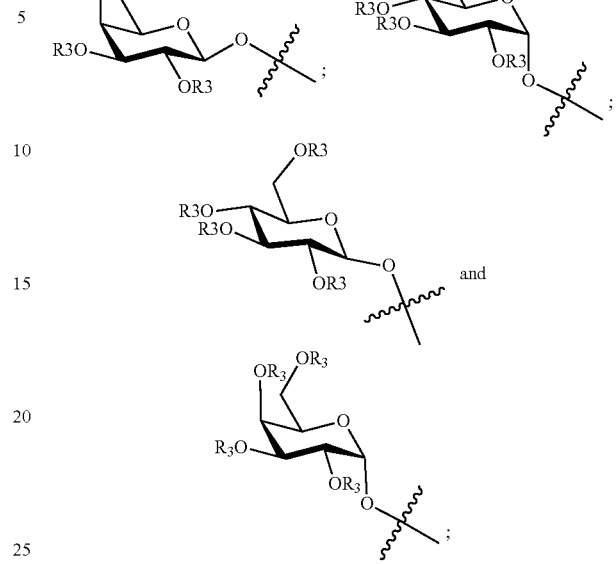
and wherein each R3 is independently H or a protecting group.

3. The compound of claim 1, or a pharmaceutically acceptable salt or solvate thereof, having the formula:

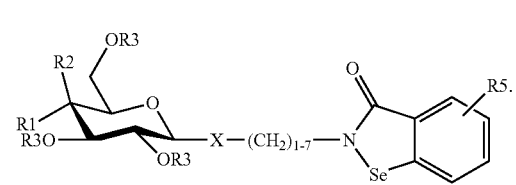

III

4. The compound of claim 3, or a pharmaceutically acceptable salt or solvate thereof, wherein one of R1 or R2 is H; and the remaining of R1 or R2 is or OR3; wherein each R3 is independently H or a protecting group.

5. The compound of claim 3, or a pharmaceutically acceptable salt or solvate thereof, wherein X is —O—, —OCO— or —NR10CO—.

6. The compound of claim 1, or a pharmaceutically acceptable salt or solvate thereof, having the formula:

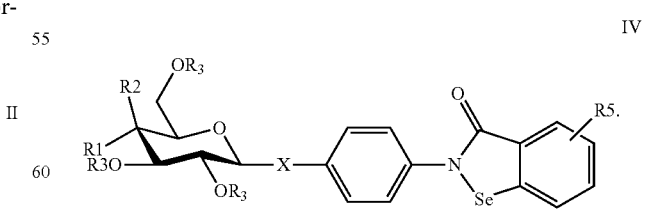

IV

7. The compound of claim 6, or a pharmaceutically acceptable salt or solvate thereof, wherein one of R1 or R2 is H; and the remaining of R1 or R2 is or OR3 or a moiety selected from the following structures:

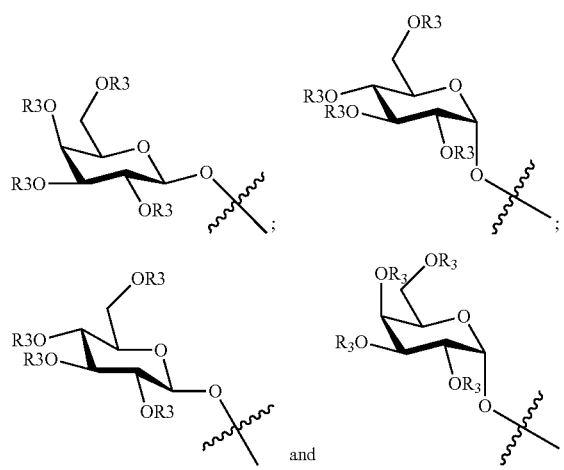
wherein each R3 is independently H or a protecting group.
8. The compound of claim 6, or a pharmaceutically acceptable salt or solvate thereof, wherein X is —O—, —OCO— or —NR10CO—.
9. The compound of claim 1, or a pharmaceutically acceptable salt or solvate thereof, wherein R3 is acetyl or H.
10. A compound selected from the group consisting of:
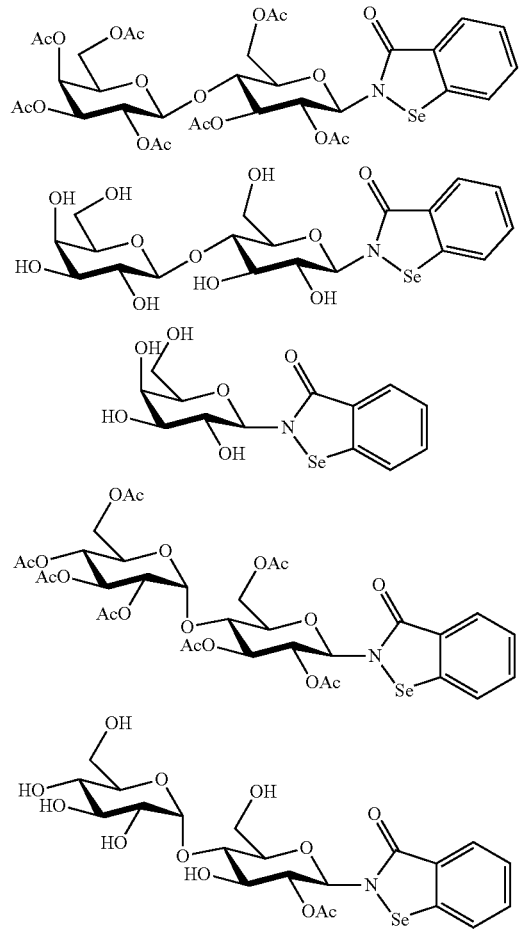
-continued
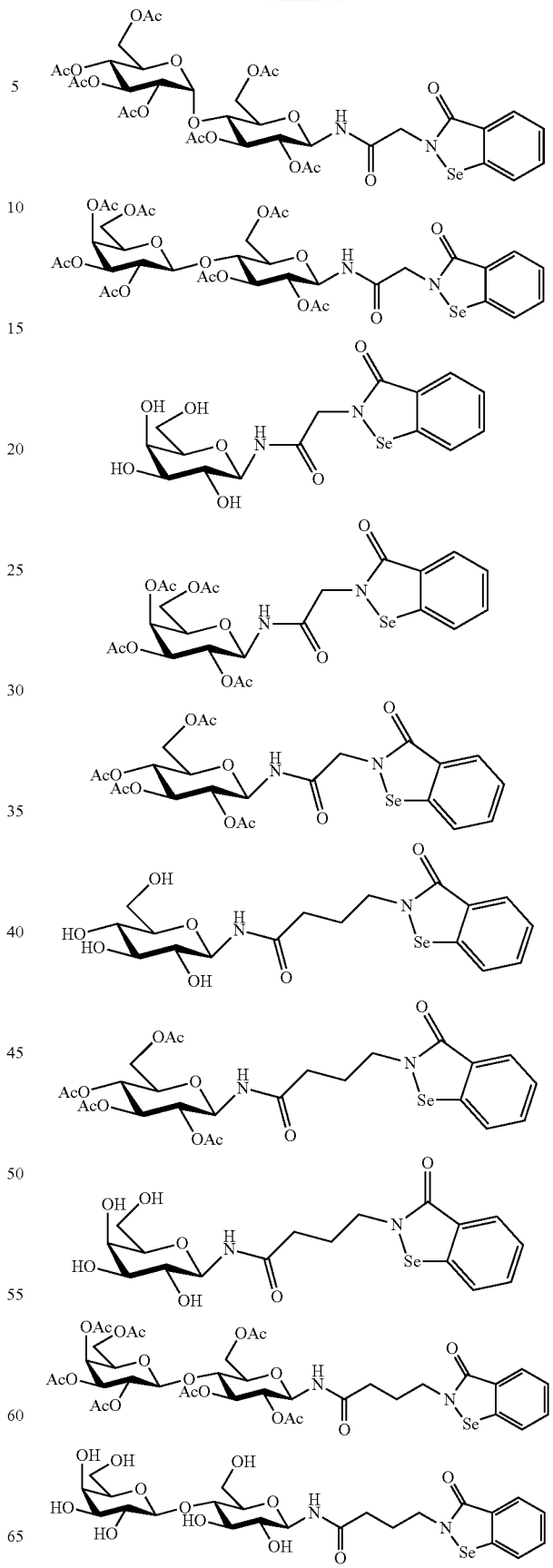

-continued

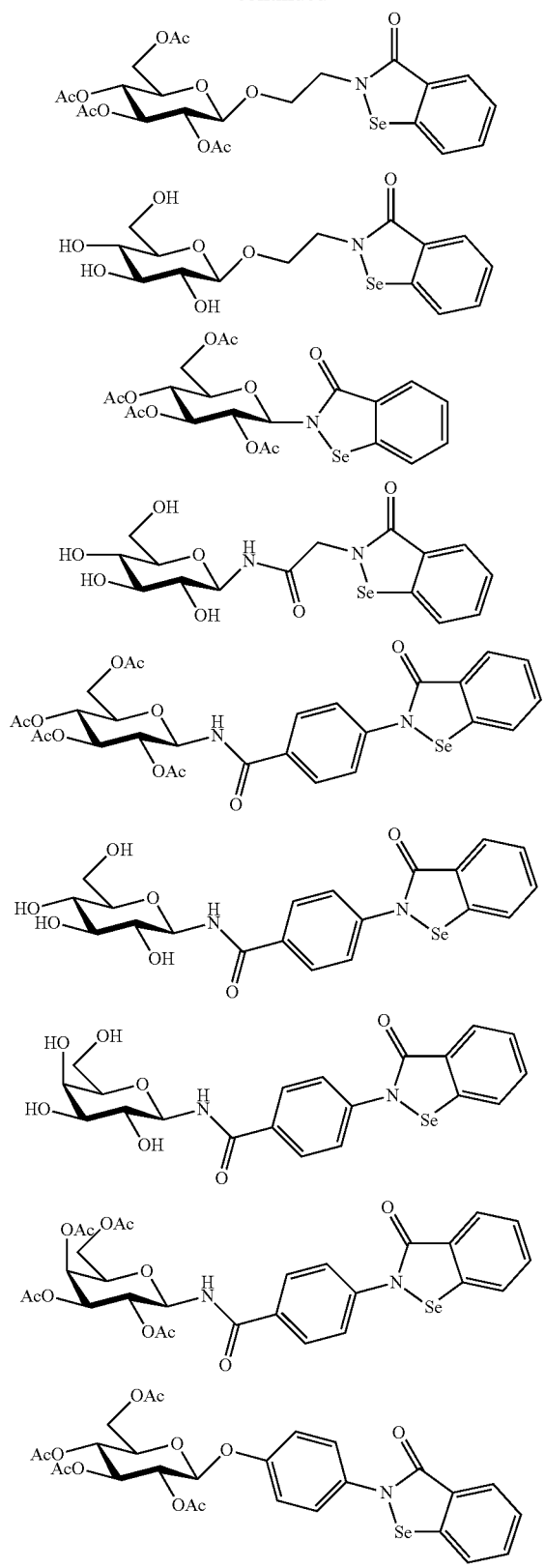

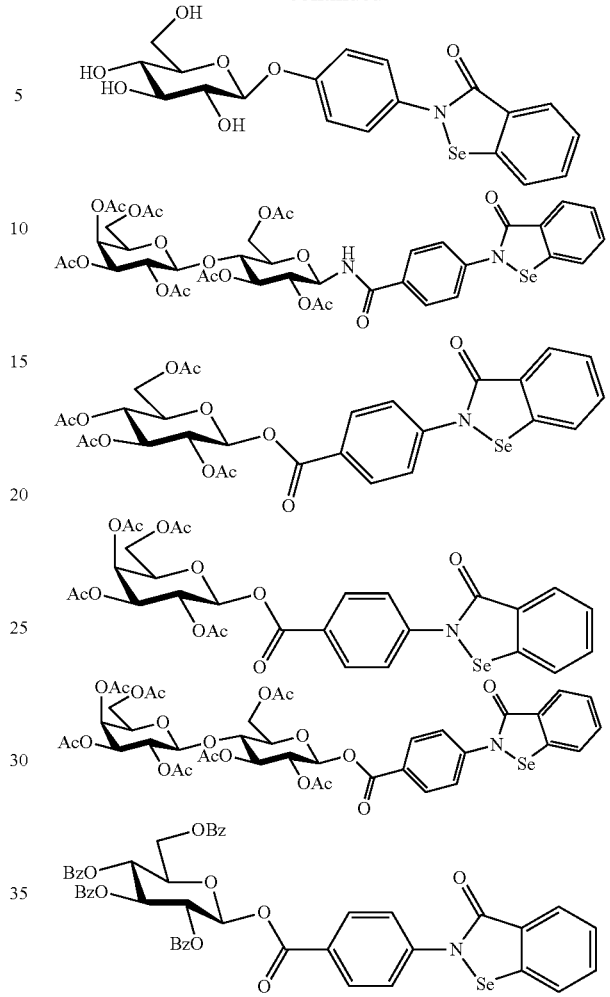

or a pharmaceutically acceptable salt or solvate thereof.

11. A pharmaceutical composition comprising a compound as defined in claim 1, or a pharmaceutically acceptable salt or solvate thereof, and an acceptable excipient.

12. A method for treating a metastatic disease in a subject in need thereof, said method comprising administering a therapeutically effective amount of the compound as defined in claim 11, or a pharmaceutically acceptable salt or solvate thereof or the pharmaceutical composition as defined in claim 12 to the subject thereby treating or preventing the metastatic disease.

13. The method of claim 12, wherein the metastatic disease is a metastatic cancer.

14. The method of claim 13, wherein the metastatic cancer is a metastatic breast cancer.

15. The method of claim 13, wherein the metastatic cancer is a metastatic colon cancer.

16. The compound of claim 4, or a pharmaceutically acceptable salt or solvate thereof, wherein X is —O—, —OCO— or —NR10CO—.

17. The compound of claim 7, or a pharmaceutically acceptable salt or solvate thereof, wherein X is —O—, —OCO— or —NR10CO—.

* * * * *